United States Patent [19]
Onda et al.

[11] Patent Number: 5,756,295
[45] Date of Patent: May 26, 1998

[54] DNA PRIMER AND A METHOD FOR SCREENING DNAS

[75] Inventors: Haruo Onda; Masaki Hosoya. both of Tsuchiura, Japan

[73] Assignee: Takeda Chemical Industries, Ltd., Osaka, Japan

[21] Appl. No.: 566,037

[22] Filed: Dec. 1, 1995

[30] Foreign Application Priority Data

Dec. 5, 1994 [JP] Japan .................... 6-300657

[51] Int. Cl.$^6$ .................... C12Q 1/68; C07H 21/02
[52] U.S. Cl. .................... 435/6; 536/23.1
[58] Field of Search .................... 435/6, 91.2; 935/77, 935/78; 530/350; 536/23.1

[56] References Cited

FOREIGN PATENT DOCUMENTS

| | | |
|---|---|---|
| 0 421 284 A1 | 4/1991 | European Pat. Off. . |
| 0 468 337 A1 | 1/1992 | European Pat. Off. . |
| 0 484 017 A2 | 5/1992 | European Pat. Off. . |
| 0 484 017 A3 | 5/1992 | European Pat. Off. . |
| 0 546 176 A1 | 6/1993 | European Pat. Off. . |
| 91/16349 | 10/1991 | WIPO . |
| 93/20204 | 10/1993 | WIPO . |
| 94/06917 | 3/1994 | WIPO . |

OTHER PUBLICATIONS

Erlich, "PCR Technology" Principles and Applications for DNA Amplification, pp. 99–104.

Onda et al., "One of the Endothelin Gene Family, Endothelin 3 Gene, is Expressed in the Placenta", FEBS Letters, vol. 261, No. 2, pp. 327–330, Feb. 1990.

Kosaka et al., "Biosynthesis of Human Endothelins in Transformants Expressing cDNAs for Human Prepro-Endothelins", The Journal of Biochemistry, vol. 116, No. 2, pp. 443–449, 1994.

Whitfeld et al., "The Human Pro-Opiomelanocortin Gene: Organization, Sequence, and Interspersion with Repetitive DNA", DNA, vol. 1, No. 2, pp. 133–143, 1982.

*Primary Examiner*—Eggerton A. Campbell
*Attorney, Agent, or Firm*—Wenderoth, Lind & Ponack

[57] ABSTRACT

DNA primers each having a nucleotide sequence substantially complementary to a nucleotide sequence which codes for Gly-Lys-Arg, Gly-Lys-Lys or Gly-Arg-Arg; methods for amplifying a polynucleotide which codes for a peptide or a precursor protein thereof using said DNA primer; screening methods for a polynucleotide which codes for a peptide comprising an amino acid sequence of Gly-Lys-Arg, Gly-Lys-Lys or Gly-Arg-Arg or a precursor protein thereof from a DNA library, etc. using said DNA; the polynucleotide obtained by said screening method; and the peptide or its precursor protein encoded by said polynucleotide, or a salt thereof. When the DNA primer of the present invention is used, the DNA which codes for a peptide having a useful physiological activity or a precursor protein thereof can be efficiently cloned.

6 Claims, 17 Drawing Sheets

FIG. 1
cDNA Insert Oriented in the Direction of Vector
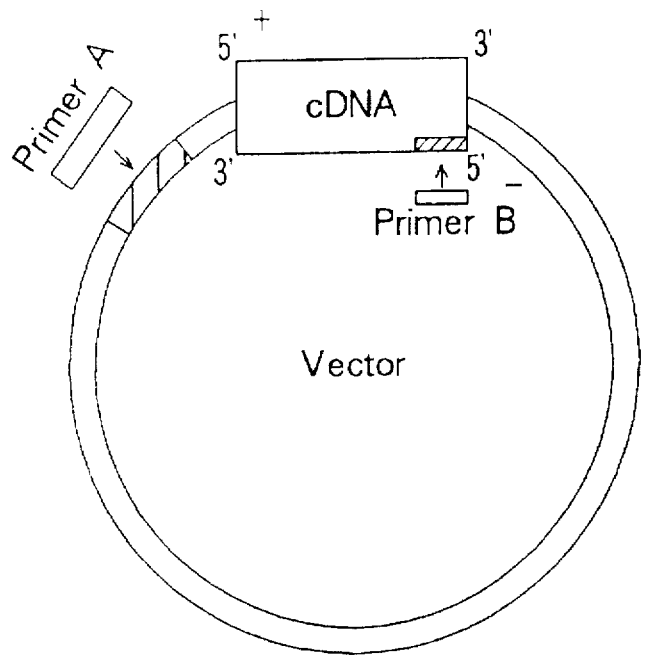
cDNA Insert Oriented in the Opposite Direction of Vector
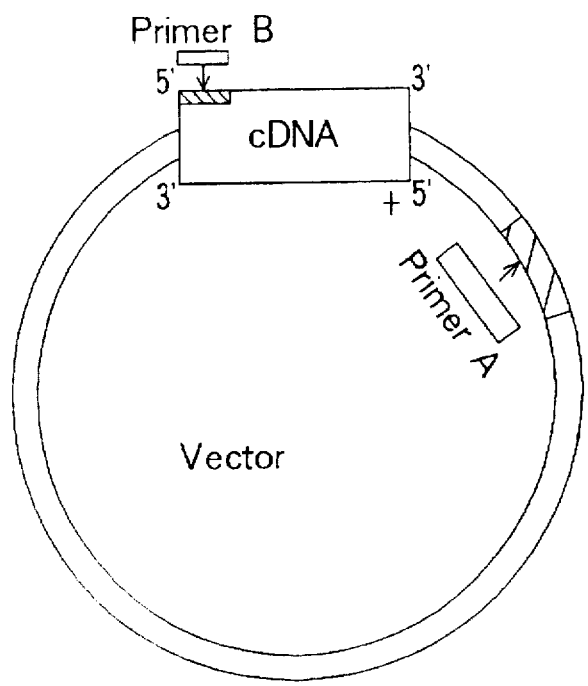

FIG. 2A

```
                                                                                                    79
CGAACCCCCCACAGCTGAGGGGCGAGGCCAGCTGTACCCGGCCCAGTGCCCTTTCGGGCCACAAGCGGCCGTCCTCCT

GGTCCGGTGCTCCGGGCCCTGATCTAGGTTC ATG GAG CCG GGG CTG TGG CTC CTT TTC GGG CTC ACA     146
                                 Met Glu Pro Gly Leu Trp Leu Leu Phe Gly Leu Thr     12

GTG ACC TCC GCC GCA GGA TTC GTG CCT TGC TCC CAG TCT GGG GAT GCT GGC AGG CGC GGC   206
    Val Thr Ser Ala Ala Gly Phe Val Pro Cys Ser Gln Ser Gly Asp Ala Gly Arg Arg Gly   32

GTG TCC CAG GCC CCC ACT GCA GCC AGA TCT GAG GGG GAC TGT GAA GAG ACT GTG GCT GGC   266
    Val Ser Gln Ala Pro Thr Ala Ala Arg Ser Glu Gly Asp Cys Glu Glu Thr Val Ala Gly   52

CCT GGC GAG GAG ACT GTG GCT CCT GGG CCT GGG GGA GAG CAG CAG GCG CCG ACA GCA CTG CAG   326
    Pro Gly Glu Glu Thr Val Ala Gly Pro Gly Gln Glu Gln Ala Pro Thr Ala Leu Gln   72

GGT CCA AGC CCT GGA AGC CGT CCT GGG CAG GAG GAG GCG GCC GAG GGG GCC CCT GAG CAC CAC   386
    Gly Pro Ser Pro Gly Ser Arg Pro Gly Gln Glu Glu Ala Ala Glu Gly Ala Pro Glu His His   92

CGA TCC AGG CGC TGC ACG TTC ACC TAC AAG GAG TGT GTC TAC TAT TGC CAC   446
    Arg Ser Arg Arg Cys Thr Phe Thr Tyr Lys Asp Lys Glu Cys Val Tyr Tyr Cys His   112

CTG GAC ATC ATT TGG ATC AAC ACT CCC GAA CAG ACG GTG CCC TAT GGA CTG TCC AAC TAC   506
    Leu Asp Ile Ile Trp Ile Asn Thr Pro Glu Gln Thr Val Pro Tyr Gly Leu Ser Asn Tyr   132

AGA GGA AGC TTC CGG GGC AAG AGG TCT CCA CTT CCA GGG CCA AAT CTG CAG CTC TCA   566
    Arg Gly Ser Phe Arg Gly Lys Arg Ser Ala Gly Pro Leu Pro Gly Asn Leu Gln Leu Ser   152

CAT CGG CCA CAC CTT CGC TGC TGT GTG GGA AGA TAT GAC AAG GCC TGC CTG CAC TTT   626
    His Arg Pro His Leu Arg Cys Cys Val Gly Arg Tyr Asp Lys Ala Cys Leu His Phe   172

TGC ACC CAA ACT CTG GAC GTT GAA CAG GTT GAA CAG GTT GAA GAC AAG AGC AAG CAG   686
    Cys Thr Gln Thr Leu Asp Val Ser Arg Gln Val Glu Asp Lys Val Lys Gln Gln Ser Lys Gln   192

GCT TTA GAC CTC CAC CAT CCA AAG CTC ATG CCC GGA AGT GGA CTC GCC GCC CTC CCA TCT   746
    Ala Leu Asp Leu His His Pro Lys Leu Met Pro Gly Ser Gly Leu Ala Leu Pro Ser   212
```

FIG. 2B

```
747  ACC TGC CCC CGC TGC CTC TTT CAG GAA GGA GCC CCT TAG GAGGACAGGCCTGCAGCATCCTGGTCTC    813
213  Thr Cys Pro Arg Cys Leu Phe Gln Glu Gly Ala Pro ***                                 225
814  GGGAGGCTTCTGCTCATTGCTGCTCACACAGTTCCACCTCTTTATAGACAAGAAGTGAATTTGCTGGGGCAGAA           893
894  CACCCACCCAAAGAGTCCCCACTTAACAATACCCCCCACGGCAAGAATGCCCAAATCCGAATGACCCAGTTTCC          973
974  TAATGAGTAAAATGATCCCAGATGTGCCCCAGAGCATGACGCCTGCAGCTCCGGTTTCATGCAGGAAATTGGTTTTGGAG   1053
1054 AGTTTTGGCAAGTTGGAAAGCCACTTACTGGCTTTGACATGACTTCTCTTGGAGAATAAGTGGACTCCAAGCTAACTCT    1133
1134 TTGCAAATGTAAACACATGTCCATTCTGTAATAAATGCAAAATGCCCGTGCAGCAGAAGCATGCGACTTTCATATCCTTG   1213
1214 CCTAGAATAGGCTGCATGGTGTATGTCAGTGAGGGCCACGAGGCGTCGGCTTTAGACACAGATCATAGCTCTACAGGAGT   1293
1294 TTATGAATTTGAAGCTTATGGGATTTTGGCAGAGAAATTTCAGTGTGCTTGATACCCACCAAAAGAATGTATCTCGAA     1373
1374 AGAATGAAGGAAGAAGAAAAAAGGATCCCTGATGTTTGTGACAAGAAAGTTAGTATCTGCAATACAGAGCTT           1463
1464 GTTCCCTGTTCAGTGACTGACCCTCTGTATTCTGTATAGACACCAGTGGAGTTCCCAGGCCTTGTTGC                1533
1534 AGGAAGCCGACTGTAAAGACAGCCCCAGCTATTAGGTTGAATATTTGCTTTCATGAGTAAATGTGGATCTTTG           1613
1614 GGGAATGGCTTCAAAATAAGTCACGAACACAAATTCTTTGTAAATTATGTAAATTCCGTTTATATAAATTGGCAACAAC    1693
1694 TTATACCGTCTGACAGTTCAAAATCTCTTTCAGCTGCGCTCTTCCCACCGAGCTGAGCTTACTGTGAGTGTGGAGATGTT   1773
1774 ATCCCACCATGTAAAGTCGCCTGCGCAGGGGAGGGCTGCCCATCTCCCAACCAGTCACAGAGAGATAGGAAACGGCAT     1863
1854 TTGAGTGGGTGTCCAGGCCCCGTAGAGAGACATTAAGATGGTGTATGACAGAGCATTGGCCTTGACCAAATGTTAAAT    1933
1934 CCCTCTGTGTATTTCATAAGTTATTACAGGTATAAAAGTGATGACCTATCATGAGGAAATGAAAGTGGCTGATTGCTG    2013
```

FIG. 2C

```
2014  GTAGGATTTTGTGTACAGTTTAGAGAAGCGATTATTTATTGTGAAACTGTTCTCCACTCCAACTCCTTTATGTGGATCTGTT  2093
2094  CAAAGTAGTCACTGTATATACGTATAGAGAGGTAGATAGGTAGATTTAAATTGCATTCTGAATACAAACTCATAC  2173
2174  TCCTTAGAGCTTGAATTACATTTTAAAATGCATATGTGCTGTTTGGCACCGTGGCAAGATGGTATCAGAGAGAAACCCA  2253
2254  TCAATTGCTCAAATACTCAGAAAGTACTGTCAAAAGCCTAATAAAA  2299
```

FIG. 10A

```
        A   A   S   D   T   G   A   S   T   A   W   S   H   R   V   Y   S   G   P   T   R
        P   P   R   I   P   G   L   P   L   P   G   H   M   V   Y   E   P   P   N
3'    R   G   F   R   D   W   R   F   H   G   M   V   Y   E   K   R   P   E
    --  --  --  --  --  --  --  --  --  --  --  --  --  --  --  --  --  --
    CGC CGG CTT AGC CAG GGT CGC CTT CAC CGG GTA CTG CAT GAA GGC CCC CAA
     9          18          27          36          45          54
    --  --  --  --  --  --  --  --  --  --  --  --  --  --  --  --  --  --
5'  GCG GCC GAA TCG GTC CCA GCG GAA GTG GCC CAT GAC GTA CTT CCG GGG GTT
    --  --  --  --  --  --  --  --  --  --  --  --  --  --  --  --  --  --

P   *   L   S   S   T   A   M   E   R   S   C   P   L   R   P   R   S
        R   D   S   A   R   W   K   G   N   G   P   V   H   S   D   R   G   L
    E   T   L   P   Q   E   D   G   N   G   P   F   M   P   T   E   A   S
    --  --  --  --  --  --  --  --  --  --  --  --  --  --  --  --  --  --
    GAG CCA GTC TCC GAC CAG CGG TAA AGG GCC CTT GTA CCC TCA GAG GGC CCG GCT
         63          72          81          90          99         108
    --  --  --  --  --  --  --  --  --  --  --  --  --  --  --  --  --  --
    CTC GGT CAG AGG CTG GTC GCC ATT TCC CGG CAT GGG AGT CTC GGC CGA
    --  --  --  --  --  --  --  --  --  --  --  --  --  --  --  --
```

FIG. 10B

```
  T   P   S   A   P   G   S   A   S   W   C   T   A   K   R   P   S   T
P   R   A   Q   L   G   P   P   H   V   G   A   P   Q   K   G   H   T   P
L   D   P   K   C   A   R   I   C   E   L   L   N   S   E   T   L
--- --- --- --- --- --- --- --- --- --- --- --- --- --- --- --- --- --- ---
CTC CAG CCC GAA CGT CCG GGC CTA CGT GAG GTC GTC CAA CGA AAG GCA CCA CTC
    117     126     135     144     153     162
--- --- --- --- --- --- --- --- --- --- --- --- --- --- --- --- --- --- ---
GAG GTC GGG CTT GCA GGC CCG GAT GCA CTC CAG CAG GTT TTC GCT CGT GGT GAG
```

```
  R   V   S   A   A   R   W   A   G   A   V   C   K   W   P   P   R   F
G   S   V   P   Q   E   G   P   V   L   W   A   S   G   H   L   G   S
D   Q   C   Q   S   E   L   C   W   G   R   V   E   M   S   A   Q
--- --- --- --- --- --- --- --- --- --- --- --- --- --- --- --- --- --- ---
CAG GAC TGT GAC CGA GAG CGT GGT CGG TGC GTG AAG TGC GTA CCT GAC
    171     180     189     198     207     216
--- --- --- --- --- --- --- --- --- --- --- --- --- --- --- --- --- --- ---
GTC CTG ACA CTG GCT CTC CTC CAG GCC ACG CAC TTC CAT GGA GGC CTG
```

FIG. 10C

```
    C   C   P   W   C   C   P   G   R   A   A   A   A   R   D   R   C   R
    A       L   G   A   V   P   G   G   L   P   Q   L   V   I   E   A   D
L                                                   R   S   C   C   S   R   P   M
--- --- --- --- --- --- --- --- --- --- --- --- --- --- --- --- --- ---
TTC GTC GTT CCG GTT GTC CCG GGG GCT CGC CGA CGT GCT AGA GCC GTA
        225         234         243         252         261         270
AAG CAG GGC CAA CAG GGC CCC CGA GCG GCA GCA TCT CGG CAT
```

```
    G   P   L   S   L   S   Q   R   P   L   S   S   E   S   P   P   S   A
    E   L   C   A   S   A   R   D   R   S   A   R   Q   P   R   P   R
K   W   A   P   Q   P   E   T   P   P   Q   E   R   L   A   P   V
--- --- --- --- --- --- --- --- --- --- --- --- --- --- --- --- --- ---
GAA GGT CCG TCC GAC TCC CCC GAG ACA GAG AGA CCG CCC CTG
        279         288         297         306         315         324
CTT CCA GGC AGG CTG CTC TGT CTC GGG AGG GGG GAC
```

FIG. 10D

```
E  R  R  R  G  A  E  R  R  E  R  P  R  D  R  P  A  R  R  E  E  K  G  G  R
S  P  A  P  P  R  A  E  E  R  P  T  A  A  R  R  E  E  K  K  G  G  R
               333         342    351         360
CGA GCC GCC GGA GAG AGC CAG CGC CGA GAA GAA GGG GGC --- 5'
GCT CGG CGG CCT CTC TCG GTC GCG GCT CTT CTT CCC CCG --- 3'
```

FIG. 11

```
         118       128       138       148       158
5' TGCAGCCGCTCGGGGGCCCTGTTGCTGGCCTTGCTGCTTCAGGCCTCCAT
   X:::::::::::::::::::::::::::::::::::::::::::::::::
5' TGCAGCCGCTCGGGGGCCCTGTTGCTGGCCTTGCTGCTTCAGGCCTCCAT
        10        20        30        40        50
         168       178       188       198       208
   GGAAGTGCGTGGCTGGTGCCTGGAGAGCAGCCAGTGTCAGGACCTCACCA
   ::::::::::::::::::::::::::::::::::::::::::::::::::
   GGAAGTGCGTGGCTGGTGCCTGGAGAGCAGCCAGTGTCAGGACCTCACCA
        60        70        80        90       100
         218       228       238       248       258
   CGGAAAGCAACCTGCTGGAGTGCATCCGGGCCTGCAAGCCCGACCTCTCG
   ::::::::::::::::::::::::::::::::::::::::::::::::::
   CGGAAAGCAACCTGCTGGAGTGCATCCGGGCCTGCAAGCCCGACCTCTCG
       110       120       130       140       150
         268       278       288       298       308
   GCCGAGACTCCCATGTTCCCGGGAAATGGCGACGAGCAGCCTCTGACCGA
   ::::::::::::::::::::::::::::::::::::::::::::::::::
   GCCGAGACTCCCATGTTCCCGGGAAATGGCGACGAGCAGCCTCTGACCGA
       160.      170       180       190       200
         318       328       338       348       358
   GAACCCCCGGAAGTACGTCATGGGCCACTTCCGCTGGGACCGATTCGGCC
   ::::::::::::::::::::::::::::::::::::::::::::::::::
   GAACCCCCGGAAGTACGTCATGGGCCACTTCCGCTGGGACCGATTCGGCC
       210       220       230       240       250

GCCGC  3'
   ::::X
   GCCGC  3'
```

FIG. 12

CSRSGALLLALLLQASMEVRGWCLESSQCQDLTTESNLLECIRA
CKPDLSAETPMFPGNGDEQPLTENPRKYVMGHFRWDRFGRRNSSSSGSSGAGQKREDV
SAGEDCGPLPEGGPEPRSDGAKPGPREGKRSYSMEHFRWGKPVGKKRRPVKVYPNGAE
DESAEAFPLEFKRELTGQRLREGDGPADDGAGAQADLEHSLLVAAEKKDEGPYRM
EHFRWGSPPPKDKRYGGFMTSEKSQTPLVTLFKNAIIKNAYKKGE 5,756,295

DNA PRIMER AND A METHOD FOR SCREENING DNAS

BACKGROUND OF THE INVENTION

1. Field of the Invention

The present invention relates to (1) a DNA primer for a polymerase chain reaction (hereinafter, briefly referred to as PCR), (2) a method for amplifying a polynucleotide such as DNA in the presence of said DNA primer, (3) a screening method for a polynucleotide, such as DNA and RNA, encoding a peptide or protein which comprises using said DNA primer, (4) a screening method for a peptide which has a useful physiological activity, a precursor protein thereof or a polynucleotide coding for said peptide or precursor protein, which comprises screening for particular C- and N-terminal amino acid sequences, (5) the polynucleotide, such as DNA and RNA, obtainable by said screening, (6) the peptide (or protein) encoded by the polynucleotide, such as DNA or RNA, which is obtainable by said screening, its precursor (or pre-mature) protein or a salt thereof, and (7) a kit for the PCR amplification and screening of said target.

2. Description of Related Art

It has been known that, in brain and nerve peptide hormones, there is a sequence comprising two basic amino acids at the side of N-terminal of the amino acid sequence of its precursor protein, while at the side of C-terminal thereof, there is a sequence comprising three amino acids as a mode of secretion of said peptide. For example, it has been known that the sequences such as Lys-Lys, Lys-Arg, Arg-Arg and Ser-Ser are present at the side of N-terminal while, at the side of C-terminal, the sequences such as Gly-Lys-Arg, Gly-Arg-Arg and Gly-Lys-Lys are present. Examples of the peptides comprising the sequences such as Gly-Lys-Arg, Gly-Arg-Arg and Gly-Lys-Lys at the side of C-terminal are as follows:

(1) C-terminal of an endothelin-1 precursor: Lys-Arg
(2) C-terminal of an endothelin-2 precursor: Lys-Lys
(3) C-terminal of an endothelin-3 precursor: Gly-Lys-Arg
(4) PACAP27: Gly-Lys-Arg (cattle, rat and human being)
(5) PACAP38: Gly-Arg-Arg (Biochem. Biophys. Res. Commun., No.3, pages 1271–1279, 1990)
(6) Adrenomedullin: Gly-Arg-Arg-Arg-Arg-Arg
(7) Proadrenomedullin: Gly-Lys-Arg
(8) LHRH: Gln-His-Trp-Ser-Tyr-Gly-Leu-Arg-Pro-Gly-Gly-Gly-Lys-Arg (Nature, 311, pages 666–668, 1984)
(9) TRH: Lys-Arg-Gln-His-Pro-Gly-Lys-Arg
(10) Secretin: Gly-Lys-Arg
(11) Arg-Vasopressin: Gly-Lys-Arg
(12) Galanin: Gly-Lys-Arg (FEBS Letters, 234, pages 400–406, 1988)
(13) VIP: Gly-Lys-Arg (DNA, vol. 4, pages 293–200, 1985)
(14) Substance P: Arg-Trp-Lys-Pro-Gln-Gln-Phe-Phe-Gly-Leu-Met-Gly-Lys-Arg (Nature, 306, pages 32–36, 1983)
(15) GLP-1 : Gly-Arg-Arg (Nature, 304, page 368, 1983)

It has been also known that, when those peptides are treated with a peptidase, matured peptide comprising precursor proteins is cleaved and secreted. Its examples are PACAP3, VIP, glucagon, galanin, TRH, LHRH and vasotocin, etc. It has been known that hormones such as calcitonin having a sequence of Gly-Lys-Lys are produced by cleavage from their precursors (Science, 213, pages 457–459, 1981).

As such, it is understood that the peptides comprising an amino acid sequence such as Lys-Lys, Lys-Arg, Arg-Arg and Ser-Ser at the side of N-terminal and comprising an amino acid sequence such as Gly-Lys-Arg, Gly-Arg-Arg and Gly-Lys-Lys at the side of C-terminal are very important physiologically active substances as the targets for proceeding a development as pharmaceuticals.

Those peptides are separated and purified using a certain activity as an index and the structures of their precursor proteins have been elucidated after cloning of cDNA using a DNA codon (prepared from a part of their amino acid sequences) as a probe. When the amino acid sequence of such a precursor protein is examined, it has been found that an amino acid sequence such as Lys-Lys, Arg-Arg, Lys-Arg and Ser-Ser at the side of N-terminal and another amino acid sequence such as Gly-Lys-Arg, Gly-Arg-Arg and Gly-Lys-Lys at the side of C-terminal are present in such a state that they sandwich the above-mentioned precursor protein.

Those peptides have been found as physiologically active substances and it is believed that there will be still many more peptides which have specific amino acid sequences at the sides of N-terminal and C-terminal. Therefore, if a peptide comprising specific amino acid sequences at the sides of N- and C-terminals can be screened selectively and efficiently, that will greatly contribute to a development of pharmaceuticals.

However, there are many difficulties in terms of the amount of starting materials, the extraction and purification, the measurement of the activity, etc. in processes for extracting and purifying a physiologically active substance of a pure state. Under such circumstances, there has been a demand for developing an effective method for cloning the DNA which codes for a physiologically active substance in an efficient manner by means of a gene engineering.

If a DNA which codes for a novel physiologically active substance can be effectively screened and isolated, then it is possible to effectively proceed the isolation of the DNA having the entire coding unit for said physiologically active substance. If the DNA which effectively codes for the physiologically active substance can be screened and then if a certain DNA which codes for the novel physiologically active substance is contained therein, it is now possible to express said DNA by means of a gene engineering and to achieve a big effect on the future research and development of pharmaceuticals.

In view of the above, it has been carried out already to screen the DNA fragments from a DNA library by means of polymerase chain reaction (PCR) using a specific DNA primer. In such a method, however, it is necessary that, after the nucleotide sequences of all of the prepared DNA fragments are analyzed, the peptides or proteins which are coded by said DNA fragment is manufactured and the physiological activity of all of such peptides is checked. Accordingly, it is essential to analyze all nucleotide sequences of the screened DNA and that requires a lot of time and labor.

In addition, with regard to the DNA primer used for the PCR, that which has a nucleotide sequence comprising 15 or more bases is usually used taking its binding ability with DNA, etc. into consideration. However, when a DNA primer having such a long nucleotide sequence is used, there is a disadvantage that an error is resulted in the complementarity with DNA whereby the DNA clone which is not aimed is screened.

In view of the above, there has been a demand for establishing a method whereby the DNA which codes for the peptide having a useful physiological activity expected for a development as a pharmaceutical agent can be selectively and effectively screened.

SUMMARY OF THE INVENTION

An object of the present invention is to provide (1) a DNA primer for PCR; (2) a method for amplification of a polynucleotide, such as DNA and RNA, in the presence of said DNA primer; (3) a screening method for a peptide or protein-encoding polynucleotide (including DNA and RNA) using said DNA primer; (4) a screening method for a physiologically or biologically useful peptide, a precursor protein thereof or a polynucleotide coding for said peptide or precursor protein, which comprises screening for particular C- and N-terminal amino acid sequences; (5) the polynucleotide, such as DNA and RNA, obtainable by said screening method; (6) a peptide or protein encoded by the polynucleotide, such as DNA or RNA, which is obtainable by said screening method, its precursor (pre-mature) protein or a salt thereof; and (7) a kit for the PCR amplification and screening of said target.

The present inventors have conducted an extensive study for solving the above-mentioned problems and found that unique techniques allow us to efficiently and specifically screen for a variety of DNAs each encoding a peptide which has a useful physiological activity or a precursor protein thereof in an early stage of a research and to isolate the same. The unique techniques include selective screening for a DNA which codes only for a peptide comprising an amino acid sequence of Gly-Lys-Arg, Gly-Arg-Arg or Gly-Lys-Lys at the C-terminal side and sequencing of said DNA followed by selection of a DNA which has a nucleotide sequence encoding at least Lys-Lys, Lys-Arg, Arg-Arg or Ser-Ser.

The present inventors have succeeded in utilizing, as a primer, a DNA which comprises a nucleotide sequence substantially complementary to a nucleotide sequence coding for Gly-Lys-Arg, Gly-Arg-Arg or Gly-Lys-Lys existing at the C-terminal side of precursor proteins such as known brain and nerve peptide hormones.

The present inventors have further succeeded in effectively amplifying a polynucleotide, such as DNA and RNA, coding for a physiologically active substance which comprises an amino acid sequence of Gly-Lys-Arg, Gly-Arg-Arg or Gly-Lys-Lys at the C-terminal side by PCR using said DNA primer.

Further, the present inventors have succeeded in effectively cloning a full length DNA (which codes for said physiologically active substance) by the use of said amplified physiologically active substance-encoding DNA, isolating and characterizing the same.

The present inventors have also found that amplification using said DNA primer and DNA sequencing of various DNAs allows us to obtain a variety of DNAs each encoding a novel physiologically active substance. The present inventors have further found that it is now possible to specifically and effectively isolate a target cDNA from a DNA library with numerous DNA clones, derived from various tissues or cells, according to the above technique by using, as primers, a DNA primer having only nine nucleotides substantially complementary to a nucleotide sequence of DNA coding for Gly-Lys-Arg, Gly-Arg-Arg or Gly-Lys-Lys and a priming sequence (primer sequence) being constructed in the DNA of a vector in which said DNA clone is established (target DNA is cloned) and to characterize the same.

An aspect of the present invention is to provide:

(1) a DNA primer comprising a nucleotide sequence substantially complementary to a template containing a nucleotide sequence coding for Gly-Lys-Arg, Gly-Arg-Arg or Gly-Lys-Lys;

(2) a method for amplifying a polynucleotide comprising a nucleotide sequence coding for Gly-Lys-Arg, Gly-Arg-Arg or Gly-Lys-Lys from a template, which comprises conducting PCR in the presence of, as a member of a primer pair, a DNA primer according to (1);

(3) a screening method for a polynucleotide containing a nucleotide sequence coding for Gly-Lys-Arg, Gly-Arg-Arg or Gly-Lys-Lys template, which comprises conducting PCR in the presence of, as a member of a primer pair, a DNA primer according to (1) and amplifying selectively said polynucleotide;

(4) a screening method for a peptide which has a useful physiological activity, a precursor protein thereof or a polynucleotide containing a nucleotide sequence coding for said peptide or precursor protein, which comprises (i) screening for C-terminal amino acids Gly-Lys-Arg, Gly-Arg-Arg or Gly-Lys-Lys; and (ii) screening for N-terminal amino acids Lys-Lys, Lys-Arg, Arg-Arg or Ser-Ser;

(5) a polynucleotide which is obtainable by a screening method according to (3) or (4), or a salt thereof;

(6) a peptide encoded by a polynucleotide according to (4) or (5), a precursor protein thereof, or a salt thereof; and (7) a kit for the PCR amplification or screening of a polynucleotide containing a nucleotide sequence coding for Gly-Lys-Arg, Gly-Arg-Arg or Gly-Lys-Lys template, which comprises a DNA primer according to claim 1 or a labeled derivative thereof.

Another aspect of the present invention is to provide the following:

(8) a DNA primer according to (1) in which said nucleotide sequence coding for Gly-Lys-Arg, Gly-Arg-Arg or Gly-Lys-Lys comprises a polynucleotide represented by any of SEQ ID NO: 1 to SEQ ID NO: 5;

(9) a DNA primer according to (1) which is a polydeoxyribonucleotide having a nucleotide sequence represented by any of SEQ ID NO: 6 to SEQ ID NO: 10;

(10) a method for amplifying a polynucleotide according to (2) in which a DNA primer for another member of said primer pair used is:

① a polynucleotide having the 5'-side nucleotide sequence of the + (plus) strand of a target DNA to be amplified or ② a polynucleotide having the 5'-side upstream nucleotide sequence of a DNA insert among the nucleotide sequences of a vector into which the target DNA to be amplified is inserted;

(11) a method for amplifying a polynucleotide according to (10) in which the DNA primer ② according to (10) is ① when the vector is a λ gt10 phage, a primer represented by d GCTGGGTAGTCCCCACCTTT (SEQ ID NO: 11) or a primer represented by d CTTATGAGTATTTCTTCCAGGGTA (SEQ ID NO: 12)

② when the vector is a λ gt11 phage, a primer represented by d GGTGGCGACGACTCCTGGAGCCCG (SEQ ID NO: 13) or a primer represented by d TTGACACCAGACCAACTGGTAATG (SEQ ID NO: 14)

③ when the vector is pUC118 or pUC119, a primer represented by d CAGGAAACAGCTATGA (SEQ ID NO: 15) or a primer represented by, d GTCGTGACTGGGAAAAC (SEQ ID NO: 16) or ④ when the vector is pcDNA1, pcDNAII, pcDNA3 or pRC/CMV, a T7 primer represented by d AATACGACTCACTATAG (SEQ ID NO: 17) or a Sp6 primer represented by d ATTTAGGTGACAC-
TATAG (SEQ ID NO: 18);

(12) a screening method according to (3) in which said DNA primer for another member of said primer pair used is
① a polynucleotide having the 5'-side nucleotide sequence of the + (plus) strand of a target DNA to be amplified or
② a polynucleotide having the 5'-side upstream nucleotide sequence of a DNA insert among the nucleotide sequences of a vector Into which the target DNA to be amplified is inserted;

(13) a screening method according to (12) in which the DNA primer ② according to (12) is
① when the vector is a λ gt10 phage, a primer represented by d GCTGGGTAGTCCCCACCTTT (SEQ ID NO: 11) or a primer represented by d CTTAT-GAGTATTTCTTCCAGGGTA (SEQ ID NO: 12)
② when the vector is a λ gt11 phage, a primer represented by d GGTGGCGACGACTCCTGGAGC-CCG (SEQ ID NO: 13) or a primer represented by d TTGACACCAGACCAACTGGTAATG (SEQ ID NO: 14)
③ when the vector is pUC118 or pUC119, a primer represented by d CAGGAAACAGCTATGA (SEQ ID NO: 15) or a primer represented by d GTCGT-GACTGGGAAAAC (SEQ ID NO: 16) or
④ when the vector is pcDNA1, pcDNAII, pcDNA3 or pRC/CMV, a T7 primer represented by d AATAC-GACTCACTATAG (SEQ ID NO: 17) or a Sp6 primer represented by d ATTTAGGTGACAC-TATAG (SEQ ID NO: 18);

(14) a screening method for a polynucleotide which codes for a peptide comprising an amino acid sequence of Gly-Lys-Arg, Gly-Arg-Arg or Gly-Lys-Lys or a precursor thereof from a template (e.g. DNA library, etc.), using PCR, which comprises selectively amplifying a polynucleotide which codes for a peptide comprising Gly-Lys-Arg, Gly-Arg-Arg or Gly-Lys-Lys at the C-terminal side or a precursor thereof, by PCR using the DNA primer according to (1) as a primer for elongating the −(minus) strand of the target DNA to be screened, from the 5' to the 3' end, in combination with:
as a primer for elongating the + (plus) strand of the target DNA to be screened, from the 5' to the 3' end,
① a DNA primer having a nucleotide sequence at the 5'-terminal side region of the + strand of the target DNA to be amplified or
② a DNA primer having a nucleotide sequence of the 5'-side upstream region of the + strand of the DNA insert among the nucleotide sequences of the vector into which the target DNA to be amplified is inserted; and

(15) a screening method for a DNA which codes for a peptide comprising not only an amino acid sequence of Lys-Lys, Lys-Arg, Arg-Arg or Ser-Ser at the N-terminal side but also an amino acid sequence of Gly-Lys-Arg, Gly-Arg-Arg or Gly-Lys-Lys at the C-terminal side or a precursor thereof from a template (e.g., DNA library, etc.), using PCR, which comprises
(i) selectively amplifying and screening a polynucleotide which codes for a peptide comprising an amino acid sequence of Gly-Lys-Arg, Gly-Arg-Arg or Gly-Lys-Lys at the C-terminal side or a precursor thereof by PCR using the DNA primer according to (1) as a primer for elongating the − strand of the target DNA to be screened from the 5' to the 3'-end, in combination with: as a primer for elongating the + strand of the target DNA to be screened from the 5' to the 3'-end,
① a DNA primer having a nucleotide sequence at the 5'-terminal side region of the + strand of the target DNA to be amplified or
② a DNA primer having a nucleotide sequence of the 5'-side upstream region of the + strand of the DNA insert among the nucleotide sequences of the vector into which the target DNA to be amplified is inserted; and
(ii) sequencing an entire nucleotide sequence of the screened polynucleotide whereby a DNA which comprises a nucleotide sequence encoding Lys-Lys, Lys-Arg, Arg-Arg or Ser-Ser at the 5'-side upstream region of the polynucleotide coding for Gly-Lys-Arg, Gly-Arg-Arg or Gly-Lys-Lys existing in said entire nucleotide sequence is selected.

As used herein, the term "substantially complementary" means homologous to or hybridizable with the designated sequence. The sequence of the region from which the polynucleotide is derived is homologous to or hybridizable with a sequence which is unique to a target nucleotide sequence (e.g., a polynucleotide coding for Gly-Lys-Arg, Gly-Arg-Arg or Gly-Lys-Lys, a polynucleotide coding for a polypeptide or protein comprising a Gly-Lys-Arg, Gly-Arg-Arg or Gly-Lys-Lys segment at the C-terminal region, a precursor thereof, etc.).

BRIEF DESCRIPTION OF THE DRAWINGS

FIG. 1 depicts the relationship between Primer A or Primer B and a vector having a target DNA insert to be amplified. The Primer A shows a DNA primer having a nucleotide sequence complementary to the nucleotide sequence at the 5'-side upstream of the + strand of the DNA insert among the nucleotide sequences of the vector. Primer B shows a DNA primer of the present invention, having a nucleotide sequence complementary to the nucleotide sequence coding for Gly-Lys-Arg, Gly-Lys-Lys or Gly-Arg-Arg.

FIG. 2 shows a nucleotide sequence of DNA coding for human endothelin-3 and a putative amino acid sequence thereof.

FIG. 10 shows a nucleotide sequence of clone No. 99 and amino acid sequences encoded by the cDNA insert wherein the DNA was read in three different reading frames.

FIG. 11 depicts a nucleotide sequence of clone No. 99 and a region ranging from the 1st to the 255th residues at the N terminal of human proopiomelanocortin-coding cDNA (the upper sequence represents the nucleotide sequence of clone No. 99 and the lower sequence represents the cDNA sequence coding for human proopiomelanocortin).

FIG. 12 depicts the amino acid sequence of human proopiomelanocortin, which corresponds to a region ranging from the -21st to the -1st amino acid residues of the signal region thereof and from the 1st to the 64th amino acid residues of the coding region thereof.

DETAILED DESCRIPTION OF THE PREFERRED EMBODIMENT

Figure 3:
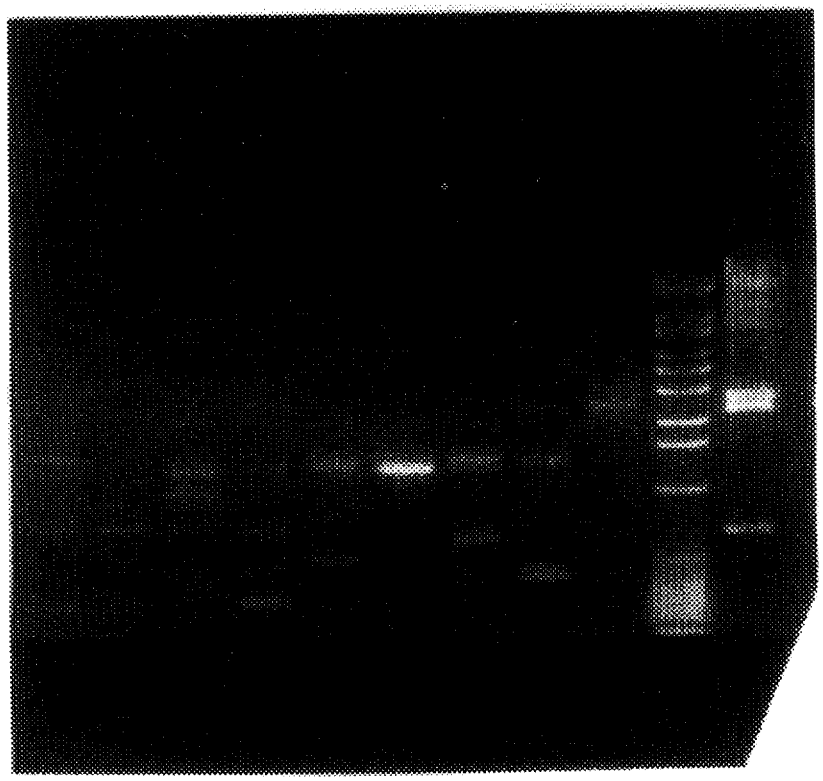
FIG. 3 is a photograph showing an electrophoresis profile of a product obtained by the PCR using template human endothelin-3 cDNA. Lane 1 shows template human endothelin-3 cDNA (100 ng/100 µl ). Ten-fold dilutions of template human endothelin-3 cDNA (100 ng/100 µl) were made sequentially, and the serial template dilutions were subjected to PCR followed by running in lanes 2 to 9. The bands in the lanes 2 to 9 show positions for the product bands. M1 shows a molecular marker of EcoRI/HindIII-digested phage DNA fragments. M2 shows a marker of HindIII-digested phage DNA fragments.

The DNA primer of the present invention is a DNA primer comprising a nucleotide sequence which is substantially complementary to (or hybridizable with) a specific nucleotide sequence coding for Gly-Lys-Arg, Gly-Arg-Arg or Gly-Lys-Lys.

Those three types of amino acid sequences are present at the C-terminal side region of mature peptides such as brain and nerve peptide hormones or precursor proteins thereof. It has been known that they are present, for example, at the C-terminal side region FIG. 1 of precursor endothelin-3 and at the C-terminal side region of precursor PACAP38. For example, Gly-Lys-Arg is present as the 138th to 140th amino acid resides in the amino acid sequence of precursor endothelin-3 (FIG. 1).

Specific examples of the nucleotide sequence coding for Gly-Lys-Arg, Gly-Arg-Arg or Gly-Lys-Lys are DNA comprising a polydeoxyribonucleotide represented by any of SEQ ID NO: 1 to SEQ ID NO: 5.

The nucleotide sequence of the DNA which codes for Gly-Lys-Arg is:

5' GGN AAR CGN 3'   (SEQ ID NO: 1)

in which N is A, T, C or G and R is A or G; or

5' GGN AAR AGR 3'   (SEQ ID NO: 2)

in which N is A, T, C or G and R is A or G).

The nucleotide sequence of the DNA which codes for Gly-Arg-Arg is:

5' GGN CGN CGN 3'   (SEQ ID NO: 3)

in which N is A, T, C or G; or

5' GGN AGR AGR 3'   (SEQ ID NO: 4)

in which N is A, T, C or G and R is A or G.

The nucleotide sequence of the DNA which codes for Gly-Lys-Lys is:

5' GGN AAR AAR 3'   (SEQ ID NO: 5)

in which N is A, T, C or G and R is A or G.

Accordingly, the DNA primer of the present invention comprising a nucleotide sequence complementary to the nucleotide sequence coding for Gly-Lys-Arg, Gly-Arg-Arg or Gly-Lys-Lys includes DNA primers comprising a nucleotide sequence complementary to each of SEQ ID NO: 1 to SEQ ID NO: 5, preferably DNA primers comprising a nucleotide sequence represented by any of SEQ ID NO: 6 to SEQ ID NO: 10, more preferably DNA primers each having any of SEQ ID NO: 6 to SEQ ID NO: 10. The DNA primer having a nucleotide sequence represented by any of SEQ ID NO: 6 to SEQ ID NO: 10 may include degenerate DNA primers which refer to plural oligo- or polynucleotides to which the incorporation of a plurality of bases, N (which means A, T, C or G) or Y (which means T or C (corresponding to R which means A or G)) leads. For example, the DNA primer having a nucleotide sequence of SEQ ID NO: 6 may be used either solely or jointly as a mixture of two or more oligo- or polynucleotides. Further, the DNA primer having a nucleotide sequence of SEQ ID NO: 6 may be used either alone or in combination with any of other DNA primers. Moreover, the DNA primer having a nucleotide sequence of any of SEQ ID NO: 6 to SEQ ID NO: 10 may be used either solely or jointly as a mixture of two or more DNA primers (e.g., as a mixture of a DNA primer having a sequence of SEQ ID NO: 6 and another DNA primer having a sequence of SEQ ID NO: 10, etc.).

5' NCG YTT NCC 3'  (SEQ ID NO: 6)

in which N is A, T, C or G and Y is T or C.

5' YCT YTT NCC 3'  (SEQ ID NO: 7)

in which N is A, T, C or G and Y is T or C.

5' NCG NCG NCC 3'  (SEQ ID NO: 8)

in which N is A, T, C or G).

5' YCT YCT NCC 3'  (SEQ ID NO: 9)

in which N is A, T, C or G and Y is T or C.

5' YTT YTT NCC 3'  (SEQ ID NO: 10)

in which N is A, T, C or G and Y is T or C.

The DNA primer of the present invention may include, but is not limited to, 9 to 50 nucleotides, preferably 9 to 30 nucleotides, more preferably 9 to 25 nucleotides, most preferably 9 to 15 nucleotides. The component nucleotide may include, but is not limited to, naturally occurring nucleic acids, synthetic nucleic acids, modified nucleic acids, and so on. The DNA primer of the present invention may be labeled. Suitable labels, and methods for labeling primers are known in the art, and include, for example, radioactive labels (e.g., incorporated by kinase), biotin, fluorescent probes, and chemiluminescent labels. The labeled DNA primer of the present invention can be prepared preferably with $^{32}P$-γ-ATP.

The DNA primer of the present invention comprising a nucleotide sequence substantially complementary to the nucleotide sequence coding for Gly-Lys-Arg, Gly-Arg-Arg or Gly-Lys-Lys may be manufactured by DNA synthesizing techniques known per se or by methods similar thereto.

The DNA primer of the present invention has a nucleotide sequence which is complementary to the nucleotide sequence coding for Gly-Lys-Arg, Gly-Arg-Arg or Gly-Lys-Lys and, therefore, it can complementarily react (be hybridized) with a template, including DNA (genome DNA, cDNA, cDNA libraries) or RNA, which codes for a peptide or its precursor protein comprising an amino acid sequence of Gly-Lys-Arg, Gly-Arg-Arg or Gly-Lys-Lys in its molecule. In addition to the DNA and RNA coding for such a peptide, it may be also complementarily bonded with a polynucleotide, such as DNA and RNA, comprising a nucleotide sequence which is similar (or homologous) to that of the DNA coding for Gly-Lys-Arg, Gly-Arg-Arg or Gly-Lys-Lys.

Accordingly, the DNA primer of the present invention can be used as a DNA primer for PCR amplification of DNA comprising a nucleotide sequence coding for the amino acid sequence represented by Gly-Lys-Arg, Gly-Arg-Arg or Gly-Lys-Lys. For example, when a PCR amplification of a small amount of template DNA is conducted wherein the DNA primer of the present invention is used as a DNA primer for one side, said template DNA can be efficiently and advantageously amplified.

In the PCR, the following are usually necessary:

(1) a combination of a DNA primer for extending a − (minus) strand of DNA coding for a C-terminal amino acid sequence from the 5' to the 3' end and a DNA primer for extending a + (plus) strand of DNA coding for a N-terminal amino acid sequence from the 5' to the 3' end; and (2) a combination of a DNA primer for extending a − (minus) strand of DNA coding for a N-terminal amino acid sequence from the 5' to the 3' end and a DNA primer for extending a + (plus) strand of DNA coding for a C-terminal amino acid sequence from the 5' to the 3' end.

The characteristic feature of the present invention is resides in initiation of selective PCR amplification from a DNA region encoding C-terminal Gly-Lys-Arg, Gly-Arg-Arg or Gly-Lys-Lys among DNA sequences which code for a peptide comprising an amino acid sequence of Gly-Lys-Arg, Gly-Arg-Arg or Gly-Lys-Lys at the C-terminal or a precursor protein thereof. Accordingly, a combination of a DNA primer for extending a − (minus) strand of DNA coding for the C-terminal amino acid sequence from the 5' to the 3' end with another DNA primer for extending a + (plus) strand of DNA coding for the N-terminal amino acid sequence from the 5' to the 3' end is preferred. Consequently, the DNA primer of the present invention (for example, the DNA primer having a nucleotide sequence represented by any of the sequences from SEQ ID NO: 6 to SEQ ID NO: 10) corresponds to a DNA primer for extending a − (minus) strand of the DNA coding for the amino acid sequence at the C-terminal side from the 5' to the 3' end.

Since the amino acid sequence of Gly-Lys-Arg, Gly-Arg-Arg or Gly-Lys-Lys is present at the C-terminal side of the target peptide or its precursor, the DNA primer of the present invention having a nucleotide sequence which is substantially complementary to the DNA coding for said amino acid sequence may be used as a DNA primer for extending the − (minus) strand of the DNA coding for the C-terminal side amino acid sequence from the 5' to the 3' end.

On the other hand, the DNA primer for extending the + (plus) strand of the DNA coding for the N-terminal amino acid sequence from the 5' to the 3' end may be any so far as it has a nucleotide sequence which is capable of being a primer for amplifying a target DNA by PCR. Examples of such a DNA primer are ①DNA primer having a 5'-side nucleotide sequence of the + strand of the target DNA to be amplified, ②a DNA primer (FIG. 1: primer A) having a nucleotide sequence at the 5'-side upstream region of the + strand of the DNA insert among nucleotide sequences of the vector into which the target DNA is inserted, etc.

Among nucleotide sequences of the vector (phage, plasmid, etc.) into which the target DNA is inserted, the DNA primer (FIG. 1: primer A) having a nucleotide sequence of the 5'-side upstream region of the + strand of the DNA insert may include:

when the vector is λ gt10 phage,

| | |
|---|---|
| d GCTGGGTAGTCCCCACCTT | (SEQ ID NO: 11), |
| d CTTATGAGTATTTCTTTCAGGGTA | (SEQ ID NO: 12), | etc.;

when the vector is λ gt11 phage,

| | |
|---|---|
| d GGTGGCGACGACTCCTGGAGCCCG | (SEQ ID NO: 13), |
| d TTGACACCAGACCAACTGGTAATG | (SEQ ID NO: 14), | etc.;

when the vector is pUC118 or pUC119,

| | |
|---|---|
| d CAGGAAACAGCTATGA | (SEQ ID NO: 15), |
| d GTCGTGACTGGGAAAAC | (SEQ ID NO: 16), | etc.; and when the vector is plasmid pcDNA1, pcDNAII, pcDNA3 or pRC/CMY, a T7 primer represented by d AATACGACTCACTATAG (SEQ ID NO: 17), an Sp6 primer represented by d ATTTAGGTGACACTATAG (SEQ ID NO: 18), etc.

PCR amplification of DNA may be carried out by conventional PCR techniques. For example, it may be carried out by the method which is disclosed in Saiki, R. K., et al: Science, 239: 487–491(1988); Ed. by H. A. Erlich, PCR Technology (Principles and Applications for DNA amplification), Stockton Press, New York, USA, 1989. Temperature, time, buffer, cycle numbers and addition of enzymes such as DNA polymerase, 2'-deoxy-7-deazaguanosine triphosphate and inosine, etc. in conducting the PCR may be suitably selected depending upon the type of target DNAs. When RNA is used as a template, a method according to Saiki, R. K., et al: Science, 239:487–491(1988) or the like may be applied.

The target template to be amplified by PCR according to the present invention may be any coding polynucleotide as long as it comprises a nucleotide sequence encoding a target peptide or protein or a precursor thereof, or even a partial peptide thereof. Examples of such a polynucleotide include DNA (which may include any of cDNA, genome DNA, cDNA library), RNA, DNA:RNA hybrids, their modified derivatives, etc. The target template may be either a DNA or RNA which codes for a known peptide or a precursor protein thereof or a DNA or RNA which codes for a novel peptide or a precursor thereof. Examples of the template are DNA or RNA which codes for a peptide or a precursor protein thereof derived from all kinds of cells and tissues (for example, pituitary gland, brain, pancreas, lung, adrenal gland, heart, placenta, umbilical cord, etc.) of vertebrates (for example, mouse, guinea pig, rat, cat, dog, swine, cattle, horse, monkey, human being, etc.), insects or other invertebrates (for example, Drosophila, silkworm (*Bombyx mori* larva) and *Barathra brassicae*), plants (for example, rice plant, wheat, tomato, etc.), cultured cell strains derived therefrom, and the like.

Said DNA library may be derived from an origin selected from the group consisting of human tissues, human cells, other warm-blooded animal tissues and cells. Examples of such human tissues include adrenal, umbilical cord, brain, tongue, liver, lymph gland, lung, thymus, placenta, peritoneum, retina, spleen, heart, smooth muscle, intestine, vessel, bone, kidney, skin, fetus, mammary gland, ovary, testis, pituitary gland, pancreas, submandibular gland, spine, prostate gland, stomach, thyroid gland, trachea (windpipe), skeletal muscle, uterus, adipose tissue, urinary bladder, cornea, olfactory bulb, bone marrow, amnion, etc. Examples of such human cells include nerve cells, epithelial cells, endothelial cells, leukocytes, lymphocytes, gliacytes, fibroblasts, keratinized cells, osteoblasts, osteoclasts, astrocytes, melanocytes, various carcinomas, various sarcomas, various cells derived from the above-mentioned human tissues.

In the PCR using the DNA primer of the present invention, the template may be any polynucleotide so far as it is a polynuclootide comprising a nucleotide sequence which encodes the peptide or protein derived from the above-mentioned tissues and cells or a precursor protein thereof. Examples of such a polynucleotide include, but are not limited to, DNA, RNA, DNA:RNA hybrids, and the like. To be more specific, it may be any of genome DNA, genome DNA library, cDNA derived from tissues/cells and cDNA library derived from tissues/cells. The DNA may be a DNA which completely codes for a peptide or a precursor protein thereof (or which comprises a full-length translation unit for said target) or may be a DNA which partially codes for a peptide or a precursor protein thereof. The DNA may also be one derived from mRNA.

The vector which is used for a library may include, but are not limited to, for example, bacteriophage, plasmid, cosmid, phagemid, etc. As mentioned already, since it is efficient to use a DNA primer having a nucleotide sequence of the 5'-side upstream region of the + strand of the DNA insert among the nucleotide sequences of the vector into which the target DNA is inserted, the DNA primer for extending the + strand of DNA coding for the N-terminal amino acid sequence of the peptide or the precursor protein thereof from the 5' to the 3' end may be preferably selected from a variety of vectors suitable for said object. For example, bacteriophages such as λ gt10 phage and λ gt11 phage; plasmids such as pUC118, pUC119, pcDNA1, pcDNAII, pcDNA3 and pRC/CMV; etc. are suitable.

It is also possible to conduct a direct amplification by RT (Reverse Transcriptase)-PCR techniques using an mRNA fraction prepared from the tisseus/cells.

Further, the DNA primer of the present invention is capable of complementarily binding (or hybridizing) with the DNA which codes for the amino acid sequence of Gly-Lys-Arg, Gly-Arg-Arg or Gly-Lys-Lys existing at the C-terminal side of the peptide or the precursor protein thereof. Accordingly, said DNA is useful as a probe to screen a DNA library for a DNA which codes for a peptide having Gly-Lys-Arg, Gly-Arg-Arg or Gly-Lys-Lys at the C-terminal side or a precursor protein thereof. The DNA probe of the present invention may be labeled. Suitable labels, and methods for labeling probes are known in the art, and include, for example, radioactive labels (e.g., incorporated by kinase), biotin, fluorescent probes, and chemiluminescent labels. The labeled DNA probe of the present invention can be prepared preferably with $^{32}$P-γ-ATP.

Screening of the DNA which codes for the peptide or the precursor thereof from a DNA library using, as a probe, the DNA primer of the present invention may be carried out by techniques known per se or by methods similar thereto. For use of such screening, the polynucleotide sample to be analyzed, such as a cDNA clone, may be treated, if desired, to extracts nucleic acids contained therein. The resulting nucleic acid from the sample may be subjected to gel electrophoresis or other size separation techniques. Alternatively, the sample extract may be dot blotted without size separation. The target polynucleotide are then visualized by hybridization with the labeled DNA probe. Especially when the DNA primer of the present invention is used as a DNA primer for PCR, both amplification and screening of the DNA which codes for the peptide or the precursor protein thereof can be conducted simultaneously.

In brief, when the DNA primer of the present invention is used as a DNA primer for one side in the PCR, said DNA primer is selectively bonded with a − strand of the DNA which codes for Gly-Lys-Arg, Gly-Arg-Arg or Gly-Lys-Lys whereupon a + strand corresponding to said − strand can be extended from the 5' to the 3' end. Therefore, when the DNA which codes for a peptide having Gly-Lys-Arg, Gly-Arg-Arg or Gly-Lys-Lys at the C-terminal said or a precursor protein thereof is selectively amplified from a DNA library, it is possible to selectively screen for said DNA.

As mentioned hereinabove, the DNA which codes for a peptide having Gly-Lys-Arg, Gly-Arg-Arg or Gly-Lys-Lys at the C-terminal side or a precursor protein thereof and which is amplified by the PCR using the DNA primer of the present invention as a DNA primer for one side can be used as it is or can be used, as desired, after modifications including connection with an adaptor having a special restriction enzyme recognition site. The resultant DNA can be subcloned by inserting into a suitable vector and, sequenced to decode its entire (e.g., "complete") nucleotide sequence. Sequencing of polynucleotides may be conducted by a commercially available sequencer.

One of the important characteristics of the screening method of DNA coding for a peptide or a precursor protein thereof by the PCR using the DNA primer of the present invention resides in the feasibility to judge that, if a clone which comprises not only a nucleotide sequence coding for three amino acids such as Gly-Lys-Arg, Gly-Arg-Arg and Gly-Lys-Lys but also a nucleotide sequence coding for two basic amino acids such as Lys-Lys, Lys-Arg, Arg-Arg and Ser-Ser at its upstream side is present among DNA clones whose entire nucleotides were sequenced by cloning, said DNA clone is a target DNA clone which codes for a peptide having a useful physiological action or a precursor protein thereof like a known and useful physiologically active substance. Thus a screening method for a peptide which has a useful physiological or biological activity, a precursor protein thereof or a polynucleotide containing a nucleotide sequence coding for said peptide or precursor protein, which comprises (i) screening for the C-terminal amino acids Gly-Lys-Arg, Gly-Arg-Arg or Gly-Lys-Lys; and (ii) screening for the N-terminal amino acids Lys-Lys, Lys-Arg, Arg-Arg or Ser-Ser, is provided. In an embodiment, the method is a determination of a polynucleotide sequence coding for a physiologically or biologically active substance which comprises (i) using the the DNA primer of the present invention to amplify a polynucleotide which comprises a nucleotide sequence coding for three amino acids, Gly-Lys-Arg, Gly-Arg-Arg or Gly-Lys-Lys by PCR or to detect said polynucleotide by hybridization and (ii) selecting a target polynucleotide which comprises not only a nucleotide sequence coding for three amino acids, Gly-Lys-Arg, Gly-Arg-Arg or Gly-Lys-Lys but also a nucleotide sequence coding for two basic amino acids, Lys-Lys, Lys-Arg, Arg-Arg or Ser-Ser at the 5'-side of the sequenced polynucleotide from the isolated polynucleotide or a cDNA library.

For example, FIG. 2 shows the nucleotide sequence of the DNA which codes for human endothelin-3 exhibiting a vasoconstrictive action and its precursor protein and the amino acid sequence deduced therefrom. In FIG. 2, Arg-Arg is present as the 95th and the 96th amino acid residues while Gly-Lys-Arg is present as the 138th to the 140th amino acid residues. As shown hereinabove, there are many cases that useful physiologically active substances or precursor thereof lie between two basic amino acid residues (e.g., Lys-Lys, Lys-Arg, Arg-Arg, Ser-Ser, etc.) at the N-terminal side and three amino acid residues (e.g., Gly-Lys-Arg, Gly-Arg-Arg, Gly-Lys-Lys, etc.) at the C-terminal side. In an embodiment, human endothelin-3 has an amino acid sequence comprising 21 amino acid residues which extend from the 97th to the 117th amino acid residues in the amino acid sequence as shown in FIG. 2.

The amino acids region between the two basic amino acid residues (e.g., Lys-Lys, Lys-Arg, Arg-Arg, Ser-Ser, etc.) at the N-terminal side thereof and the three amino acid residues (e.g., Gly-Lys-Arg, Gly-Arg-Arg, Gly-Lys-Lys, etc.) at the C-terminal side may include, but is not limited to, preferably 2 to 70 amino acids more preferably 3 to 50 amino acids.

According to the present invention, it is possible to select a DNA clone encoding a novel matured peptide which is expected to exert a useful physiological and biological activity or a precursor thereof at an early stage from the DNA clones which are screened by PCR using the subject DNA primer.

When the DNA clone obtained by the above-mentioned screening method is a DNA which partially codes for the peptide or the precursor protein thereof, it is possible to screen the DNA library for DNA which completely codes for the physiologically active substance by a known method per se using as a probe said DNA clone. Such probes may be labeled. Suitable labels, and methods for labeling probes are known in the art, and include, for example, radioactive labels (e.g., incorporated by kinase), biotin, fluorescent probes, and chemiluminescent labels.

Cloning of the DNA is conducted either by PCR amplification using a synthetic DNA primer having a partial nucleotide sequence of said DNA or by hybridization with a labeled DNA having a partial or full-length region of said DNA or a labeled synthetic DNA followed by selection. The hybridization may be carried out, for example, by techniques disclosed in "Molecular Cloning" 2nd ed.; Maniatis, et al., Cold Spring Harbor Laboratory Press, 1989. When a commercially available library is used, the hybridization is conducted according to protocols or manuals attached thereto.

The present invention provides a method for an efficient and selective screening of DNA or RNA which codes for a peptide having the three amino acids of Gly-Lys-Arg, Gly-Arg-Arg or Gly-Lys-Lys at the C-terminal side or a precursor thereof from a template including a DNA library, an RNA library derived from tissues/cells, etc., which comprises using the DNA primer of the present invention as a DNA primer for one side in the PCR.

In an embodiment of the present invention, the PCR is conducted using the DNA primer of the present invention as a DNA primer for one side in the PCR in combination with another DNA primer having a nucleotide sequence at the 5'-side upstream region in the + strand of the DNA insert among the nucleotide sequences of a vector into which a template DNA is inserted, whereupon the DNA which codes for a peptide having Gly-Lys-Arg, Gly-Arg-Arg or Gly-Lys-Lys at the C-terminal side or a precursor protein thereof is amplified and selected (i.e., screened) to analyze a whole nucleotide sequence of said DNA. Then the DNA having a nucleotide sequence which codes for the two basic amino acids, i.e. Lys-Lys, Lys-Arg, Arg-Arg or Ser-Ser, in the strand is selected as a candidate for DNA coding for a peptide having a useful physiological activity or a precursor protein thereof. In addition, if the selected DNA is found to be a DNA which partially codes for the peptide or its precursor protein, the present invention provides a method for cloning DNA which completely codes for said peptide or its precursor protein from a DNA library, etc.

In the screening method for DNA encoding the peptide or its precursor in accordance with the present invention, the target DNA or RNA includes subjects which are same as the template including DNA, RNA and a library thereof used for the above-mentioned amplification of the DNA according to the present invention.

As mentioned above, when the DNA primer having nine bases encoding only three amino acid residues (Gly-Lys-Arg, Gly-Arg-Arg or Gly-Lys-Lys) for one side in the PCR is used according to the present invention, it is possible to selectively and efficiently screen for a variety of DNAs each of which codes for a peptide having an amino acid sequence: Gly-Lys-Arg, Gly-Arg-Arg or Gly-Lys-Lys at the C-terminal side or a precursor protein thereof. Moreover, when a nucleotide sequence of the DNA obtained by the screening is analyzed, it is possible to effectively and advantageously select specific DNA coding for a peptide characteristically comprising two amino acid residues, i.e., Lys-Lys, Lys-Arg, Arg-Arg or Ser-Ser, at the N-terminal side or a precursor protein thereof. It is also possible to selectively and efficiently screen for various DNAs each of which codes for a novel specific peptide having a useful physiological activity and comprising not only specific two basic amino acid residues, i.e., Lys-Lys, Lys-Arg, Arg-Arg, Ser-Ser, etc., at the N-terminal side but also specific three amino acid residues, i.e., Gly-Lys-Arg, Gly-Arg-Arg or Gly-Lys-Lys, at the C-terminal side or a precursor protein thereof.

The DNA primers and probes of the present invention can be packaged into reagent kits for PCR and screening. Reagent kits for PCR include the DNA primer, which may be labeled or unlabeled. The kit may contain other suitably packaged reagents and materials needed for the particular PCR amplification protocol, for example, enzymes, standards, buffering agents, as well as instructions for conducting the reaction. The kit may also contain another member of primer pair such as a primer for elongating the + strand of the target DNA to be screened from the 5' to the 3'-end. The kit ingredients may be included in the kit in separate containers. Reagent kits for screening include the DNA primer or probe, which may be labeled; alternatively the DNA primer and probe may be unlabeled and the ingredients for labeling may be included in the kit in separate containers. The kit may also contain other suitably packaged reagents and materials needed for the particular hybridization protocol, for example, markers, as well as instructions for conducting the selection. Kits suitable for PCR amplification and screening of a target containing the labeled or unlabeled reagents are constructed by packaging the appropriate materials, including the DNA primer of the present invention in suitable containers, along with the remaining reagents and materials required for the conduct of the reaction or isolation, as well as a suitable set of manipulation instructions.

Moreover, according to the present invention, it is possible to clone cDNA which codes for a novel peptide or a precursor protein thereof by the following method:

For example, cDNA is synthesized using a DNA primer comprising nine bases which code for those three amino acids (Gly-Lys-Arg, Gly-Arg-Arg or Gly-Lys-Lys) and template mRNA, followed by digestion of the template RNA with an alkali. Then, any of oligo(dA), oligo(dT), oligo(dG) and oligo(dC) is added to the 3' end of a single-stranded DNA with a terminal transferase. Then a double-stranded DNA is synthesized using, as a primer, oligo(dX) (corresponding to said oligo(dX) added thereto), i.e., oligo (dT), oligo(dA), oligo(dC) or oligo(dG)). A treatment with T4 polymerase is conducted to blunt end the 5'- and 3'-ends of the single-stranded DNA and a kinase reaction is conducted to phosphorylate the 5'-termini. EcoRI adaptor DNA fragments are ligated with the resultant DNA followed by cloning to the EcoRI site of a vector such as phage or plasmid. Then the cloned DNA is subjected to DNA sequencing analysis and, if there are DNA codons for the two basic amino acid residues, i.e. Arg-Arg, Lys-Lys, Lys-Arg, Ser-Ser, etc. at the 5'-terminal upstream, there is a high possibility that said cDNA is a cDNA which codes for a peptide (or a precursor thereof) comprising not only two basic amino acid residues, i.e., Lys-Lys, Lys-Arg, Arg-Arg or Ser-Ser, at the N-terminal side but also three amino acid residues, i.e. Gly-Lys-Arg, Gly-Arg-Arg or Gly-Lys-Lys, at the C-terminal side. Said cDNA having such a specific sequence can be confirmed by means of a recloning from a DNA library.

The screening in accordance with the present invention in which the DNA primer of the present invention is used as a DNA primer for one side in the PCR is far more efficient than a method in which a cDNA clone is randomly sequenced and analyzed prior to selecting cDNA coding for a physiologically active substance. Because, even if the nucleotide sequence of the cDNA is randomly analyzed, there is a very low possibility that the DNA clone having not only DNA codons for Arg-Arg, Lys-Lys, Lys-Arg or Ser-Ser at the 5'-side but also DNA codons for Gly-Lys-Arg, Gly-Arg-Arg or Gly-Lys-Lys at the 3'-side is contained in said cDNA clones. The reasons are that, since a random primer and oligo(dT) primer are used for preparing a cDNA library, the possibility for producing the cDNA which specifically codes for a peptide having such a specific sequence or a precursor protein thereof is significantly reduced and also that, even when the cDNA fragments which code for such a peptide or a precursor protein thereof is produced, said cDNA cannot be concluded to be a cDNA which codes for a peptide having a useful physiological activity or a precursor protein thereof if the DNA codons for Arg-Arg, Lys-Lys, Lys-Arg or Ser-Ser at the 5'-side and that for Gly-Lys-Arg, Gly-Arg-Arg or Gly-Lys-Lys at the 3'-side of said cDNA are not found.

The target peptide or its precursor protein-encoding DNA obtained by the screening method of the present invention can be used as it is, or can be used, as desired, after modifications including digestion with a restriction enzyme or addition of a linker or adapter, etc. depending upon objects. The DNA may have an initiation codon, ATG, on the 5' terminal side and a termination codon, TAA, TGA or TAG, on the 3' terminal side. These initiation and termination codons can be ligated by using a suitable synthetic DNA adapter. In addition, determination of tissues/cells in which said physiologically active substance is expressed may be performed by northern blotting using said DNA as a probe. Further, when the DNA having a full-length open reading frame (ORF or complete translation unit) is ligated with a suitable promoter and introduced into animal cells, the physiologically active substance can be expressed. It is also possible that said peptide or its precursor protein is subjected to various biological assessment systems to reveal its physiological activity.

The peptides and their precursor proteins according to the present invention and salts thereof are peptides each having an amino acid sequence encoded by the polynucleotide (e.g., DNA) obtained by the above-mentioned screening method or precursor proteins thereof or salts thereof.

The peptide and its precursor of the present invention may be manufactured by culturing a transformant carrying DNA coding for said peptide or a precursor protein thereof or may be manufactured by peptide synthesis. Alternatively, it may be isolated from tissues or cells of warm-blooded animals by techniques for protein purification known per se. Methods of synthesizing peptide may be any of a solid phase synthesis and a liquid phase synthesis. Thus, a partial peptide (peptide fragment) or amino acids which can construct the protein or its precursor according to the present invention is condensed with a residual part thereof and, when the product has a protective group, said protective group is removed to manufacture the desired peptide or its precursor protein. Examples of the known methods for condensation and for removal of protective groups include the following ①to ⑤:

①M. Bodanszky and M. A. Ondetti: Peptide Synthesis, Interscience Publishers, New York (1966).

②Schroeder and Luebke: The Peptide, Academic Press, New York. (1965).

③Nobuo Izumiya et al.: Fundamentals and Experiments of the Peptide Synthesis, Maruzen KK, Japan (1975).

④Haruaki Yajima and Shumpei Sakakibara: "Seikagaku Jikken Koza 1" (Experiments of Biochemistry, Part 1), "Tanpakusitu No Kagaku IV" (Chemistry of Protein, IV), p.205 (1977), Japan.

⑤Haruaki Yajima (ed): Development of Pharmaceuticals (Second Series), Vol. 14, Peptide Synthesis, Hirokawa Shoten, Japan.

After the reaction, conventional purifying techniques such as salting-out, extraction with solvents, distillation, column chromatography, liquid chromatography, electrophoresis, recrystallization, etc. are optionally combined to separate, isolate and purify the peptide or its precursor protein of the present invention or a thereof. When the protein obtained as such is a free compound, it may be converted to a suitable salt by known methods while, when it is obtained as a salt, the salt may be converted to a free compound or other salt compounds by known methods.

The salt of said peptide or its precursor protein of the present invention includes preferably physiologically acceptable acid addition salts. Examples of such salts are salts thereof with inorganic acids (e.g. hydrochloric acid, phosphoric acid, hydrobromic acid, sulfuric acid, etc.), salts thereof with organic acids (e.g. acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.), etc.

In revealing the physiological activity of the peptide or its precursor protein of the present invention, it may be subjected to an assessment system for various biological activities.

For example, the peptide or its precursor protein of the present invention is added to cells derived from original cells or tissues wherefrom the cDNA library is prepared and its physiological activity can be assessed in vitro by observing the propagation of cells, the change of intracellular Ca concentration, the change of cyclic AMP concentration, etc.; by checking the change of endocellular or extracellular secreted substances, etc.; or by investigating muscle contraction reaction in vitro. Further, if the reaction is positive in said in vitro assessment system, the peptide or its precursor protein is administered to animals, e.g., by injection, etc. for checking in vivo reactions and responses such as the changes of blood pressure or endocrine systems are measured whereby the in vivo physiological activity of the peptide or its precursor protein of the present invention can be clarified.

The peptide of the present invention or the precursor protein thereof may be used as a pharmaceutical composition depending upon its physiological action. The compound or the salt thereof may be orally, parenterally, rectally, or topically administered as pharmaceutical compositions or formulations (e.g. powders, granules, tablets, pills, capsules, injections, syrups, emulsions, elixirs, suspensions, solutions, etc.). For example, it may be used orally as optionally sugar-coated tablets, capsules, elixirs, microcapsules, etc. or may be used parenterally as aseptic solutions with water or with other pharmaceutically acceptable liquids or as injections such as suspensions. They are manufactured, for example, by mixing said peptide, its precursor or a salt thereof with a physiologically acceptable carrier, fragrance, filler, vehicle, antiseptic agent, stabilizer, binder, etc. in a dose unit form which is commonly approved and required in preparing the pharmaceutical preparations. An amount of the effective component in those preparations is to be in such an extent that the suitable dose within an indicated range is achieved.

Examples of the additives which can be admixed in the tablets, capsules, etc. are binders such as gelatin, corn starch, tragacanth and gum arabicum; fillers such as crystalline cellulose; swelling agents such as corn starch, gelatin and alginic acid; lubricants such as magnesium stearate; sweetening agents such as sucrose, lactose and saccharine; preservatives such as parabens and sorbic acid; antioxidants such as ascorbic acid, $\alpha$-tocopherol and cysteine; fragrances such as peppermint, akamono oil and cherry; disintegrants; buffering agents; etc. Other additives may include mannitol, maltitol, dextran, agar, chitin, chitosan, pectin, collagen, casein, albumin, synthetic or semi-synthetic polymers, glyceride, lactide, etc. When the unit form of the preparation is a capsule, a liquid carrier such as fat/oil may be further added besides the above-mentioned types of materials. The aseptic composition for injection may be formulated by a conventional technique or practice for the preparations such as that the active substance in a vehicle such as water for injection is dissolved or suspended in a naturally occurring plant oil such as sesame oil and palm oil.

Examples of an aqueous liquid for the injection are a physiological saline solution and isotonic solutions containing glucose and other auxiliary agents (e.g. D-sorbitol, D-mannitol, sodium chloride, etc.) wherein a suitable auxiliary solubilizers such as alcohol (e.g. ethanol, etc.), polyalcohol (e.g. propylene glycol, polyethylene glycol, etc.), nonionic surface-active agent (e.g. Polysorbate 80™, HCO-50, etc.), etc. may be jointly used. In the case of the oily liquid, sesame oil, soybean oil, etc. may be exemplified wherein benzyl benzoate, benzyl alcohol, etc. may be jointly used as auxiliary solubilizers.

In addition, buffers (e.g. phosphate buffer, sodium acetate buffer, etc.), analgesic agents (e.g. benzalkonium chloride, procaine hydrochloride, etc.), stabilizers (e.g. human serum albumin, polyethylene glycol, etc.), stabilizers (e.g. benzyl alcohol, phenol, etc.), antioxidants, etc. may be compounded therewith too. The prepared injection solution is filled in suitable ampoules. The formulation prepared as such is safe and less toxic and, therefore, it can be administered to warm-blooded mammals such as rats, rabbits, sheep, swines, cattle, cats, dogs, monkeys, human being, etc.

Dose levels of said pharmaceutical formulations or preparations may vary depending upon the symptom. Specific dose levels for any particular patient will be employed depending upon a variety of factors including the activity of specific compounds employed, the age, body weight, general health, sex, diet, time of administration, route of administration, rate of excretion, drug combination, and the severity of the particular disease undergoing therapy.

In the case of oral administration, it is usually about 0.1–100 mg, preferably about 1.0–50 mg or, more preferably, about 1.0–20 mg per day for adults (as 60 kg). When it is administered parenterally, its dose at a time may vary depending upon the object to be administered, organs to be administered, symptoms, administering methods, etc. The term "parenteral" as used herein includes subcutaneous injections, intravenous, intramuscular, intraperitoneal injections, or infusion techniques. In the case of injections, it is usually convenient to give by an intravenous route in an amount of about 0.01–30 mg, preferably about 0.1–20 mg or, more preferably, about 0.1–10 mg per day to adults (as 60 kg). In the case of other animals, the dose calculated for 60 kg may be administered as well.

The DNA primer of the present invention is a DNA primer comprising a nucleotide sequence substantially complementary to the nucleotide sequence coding for Gly-Lys-Arg, Gly-Lys-Lys or Gly-Arg-Arg.

When the PCR using the DNA primer of the present invention is carried out, a DNA which codes for a peptide having Gly-Lys-Arg, Gly-Lys-Lys or Gly-Arg-Arg at the C-terminal side can be efficiently and advantageously amplified. When this amplification is used, a DNA coding for a physiologically active substance comprising Gly-Lys-Arg, Gly-Lys-Lys or Gly-Arg-Arg at the C-terminal region can be efficiently and effectively screened and cloned.

Further, if a nucleotide sequence coding for the two basic amino acid residues (Lys-Lys, Lys-Arg, Arg-Arg or Ser-Ser) can be found in the full length nucleotide sequence of the cloned target DNA, it is confirmed that said DNA is a DNA encoding a physiologically active substance.

In the specification and drawings of the present application, the abbreviations used for bases (nucleotides), amino acids and so forth are those recommended by the IUPAC-IUB Commission on Biochemical Nomenclature or those conventionally used in the art. Examples thereof are given below. Amino acids for which optical isomerism is possible are, unless otherwise specified, in the L form.

DNA : Deoxyribonucleic acid
cDNA: Complementary deoxyribonucleic acid
A : Adenine
T : Thymine
G : Guanine
C : Cytosine
RNA : Ribonucleic acid
mRNA : Messenger ribonucleic acid
dATP: Deoxyadenosine triphosphate
dTTP: Deoxythymidine triphosphate
dGTP: Deoxyguanosine triphosphate
dCTP: Deoxycytidine triphosphate
ATP : Adenosine triphosphate
EDTA: Ethylenediamine tetraacetic acid
SDS : Sodium dodecyl sulfate
EIA: Enzyme Immunoassay
G, Gly: Glycine (or Glycyl)
A, Ala: Alanine (or Alanyl)
V, Val: Valine (or Valyl)
L, Leu: Leucine (or Leucyl)
I, Ile: Isoleucine (or Isoleucyl)
S, Ser: Serine (or Seryl)
T, Thr: Threonine (or Threonyl)
C, Cys: Cysteine (or Cysteinyl)
M, Met: Methionine (or Methionyl)
E, Glu: Glutamic acid (or Glutamyl)
D, Asp: Aspartic acid (or Aspartyl)
K, Lys: Lysine (or Lysyl)
R, Arg: Arginine (or Arginyl)
H, His: Histidine (or Histidyl)
F, Phe: Pheylalanine (or Pheylalanyl)
Y, Tyr: Tyrosine (or Tyrosyl)
W, Trp: Tryptophan (or Tryptophanyl)
P, Pro: Proline (or Prolyl)
N, Asn: Asparagine (or Asparaginyl)
Q, Gln: Glutamine (or Glutaminyl)

The practice of the present invention will employ, unless otherwise indicated, conventional techniques of molecular biology, microbiology, recombinant DNA, genetic engineering, pharmacology, immunology, biochemistry, bioscience, and medical technology, which are within the skill of the art. Such techniques may also be referred to each of the series of "Methods in Enzymology, Academic Press, Inc." All documents, and publications mentioned herein, both supra and infra, are hereby incorporated herein by reference.

EXAMPLES

Described below are examples of the present invention which are provided only for illustrative purposes, and not to limit the scope of the present invention. In light of the present disclosure, numerous embodiments within the scope of the claims will be apparent to those of ordinary skill in the art.

Example 1

Screening of Human Endothelin-3 cDNA.

(1) Screening of Human Endothelin-3 cDNA.

In the nucleotide sequence of human endothelin-3 precursor as reported by Otoda, et al., it was found that a nucleotide sequence of GGC AAG AGG (SEQ ID NO: 19) from the 521st to the 530th nucleotides therein is present and it codes for three amino acids, Gly-Lys-Arg. In addition, it was found that a nucleotide sequence of AGG CGC from the 393rd to the 398th nucleotides therein is also present and it codes for two amino acids, Arg-Arg (FIG. 2) (FEBS Letters, 261, 327–330(1990)).

For human endothelin-3, it is presumed that big endothelin-3 (precursor endothelin) comprising 42 amino acids is cleaved with an endothelin converting enzyme at the next bond after the 21st amino acid, Trp, of the precursor endothelin-3 to produce a mature endothelin-3 (comprising 21 amino acid residues as surrounded by brackets in FIG. 2; cf. Kosaka, et al., Journal of Biochemistry, 116, 443–449, 1994).

This big endothelin-3 is sandwiched between an amino acid sequence (Arg-Arg) immediately in front of the terminal Cys and another amino acid sequence (Gly-Lys-Lys) at the C-terminal side of endothelin-3. Now, as is described below, the following example of human endothelin-3 (hereinafter, briefly referred to as human ET-3) illustrates an embodiment of the present invention. Human ET-3 1DNA was specifically cloned as a cDNA having the two basic amino acid residues (Lys-Lys, Lys-Arg, Arg-Arg or Ser-Ser) at the N-terminal side and an amino acid sequence (Gly-Lys-Arg, Gly-Arg-Arg or Gly-Lys-Lys) at the C-terminal side.

In order to confirm that PCR can be carried out in the presence of a DNA primer having a nucleotide sequence complementary to the nine nucleotides coding for the amino acid residues (Gly-Lys-Arg), the operations are conducted. Briefly, a cDNA fragment was cut out from pHET-3(P) (which is a cDNA clone of human ET-3) with restriction enzyme EcoRI and was electrophoresed on 4% acrylamide gel. An aliquot (100 ng) of purified cDNA was used for conducting PCR using a reaction solution of the following composition.

| Reaction Solution: Composition A: | |
|---|---|
| Template: Human ET-3 cDNA 100 ng × 10⁻⁸ | 10 μl |
| Primer: 5' CCT CTT GCC 3' (SEQ ID NO: 20) | 1 μl |
| PCR × 10 buffer | 10 μl |
| dXTP Solution: 2.5 mM | 10 μl |
| Taq DNA Polymerase | 1 μl |
| Distilled water | 68 μl |
| Total | 100 μl | dXTP: Deoxyribonucleotide triphosphates (dATP, dCTP, dGTP & dTTP)

The conditions for the PCR were:
Each cycle consisted of incubation at 94° C. for 1 min., incubation at 36 ° C. for 1 mi. and incubation at 72° C. for 2 min. and 46 cycles were conducted. The device used for the PCR was a Perkin-Elmer Type DNA Thermal Cycler (Cetus, USA).

Then, in order to analyze PCR DNA products which were synthesized by this PCR, 25 μl of the reaction solution was taken out, subjected to an electrophoresis with 1% agarose gel and stained with ethidium bromide. The resulting pattern is given in FIG. 3.

The PCR product of this reaction was supposed to be a minus strand (with 530 nucleotides) of single-stranded human ET-3 cDNA comprising 530 bases. In FIG. 3, it is hard to judge only from the ethidium bromide-stained chart whether the DNA product of such a size was synthesized. Accordingly, hybridization using, as a probe, human ET-3 cDNA was conducted after transferring this synthesized single-stranded DNA to a nitrocellulose filter (southern transfer).

The probe used for the hybridization was obtained by nick labeling a DNA fragment of the human ET-3 cDNA (used as a template) with $^{32}$P-dCTP.

Figure 4:
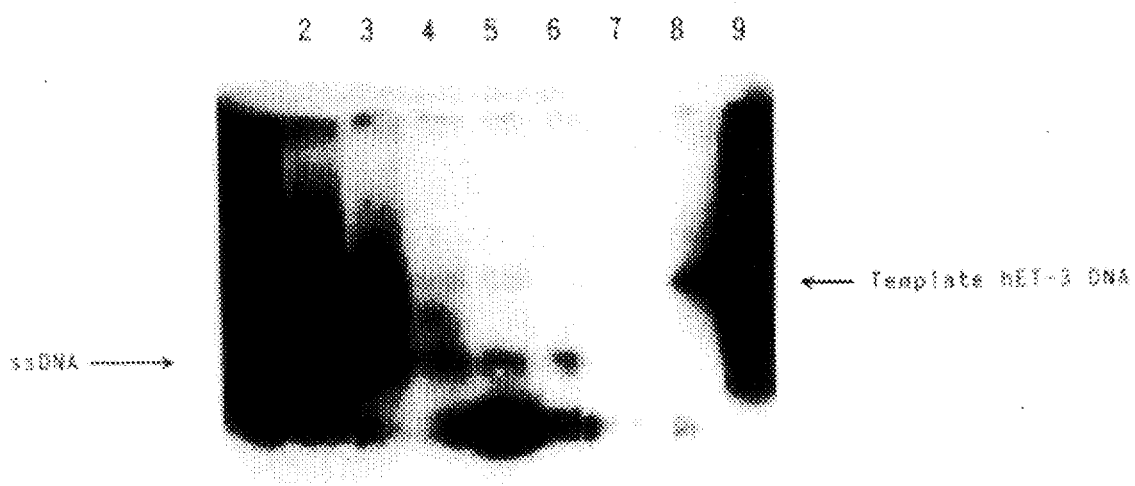
FIG. 4 is a photograph showing a southern hybridization profile of labeled human endothelin-3 cDNA with a single-stranded human endothelin-3 cDNA (ssDNA) obtained by PCR using, as a template, human endothelin-3 cDNA (template hET-3). Ten-fold dilutions of template human endothelin-3 cDNA (100 ng/100 µl) were made sequentially, and the serial template dilutions were subjected to PCR followed by running in lanes 2 to 8. An arrow in the lane 9 shows a band position for template human endothelin-3 cDNA. Arrows of the lanes 2 to 8 show band positions for the single-stranded DNA (ssDNA) samples.

The filter was subjected to an autoradiography and the result is given in FIG. 4. As shown in FIG. 4, the bands indicated by an arrow were detected depending upon the concentrations of template human ET-3 cDNA. A band with a size of 530 bases or more but being shorter than the 2,299 base template was confirmed.

This PCR DNA product was a single-stranded DNA which was synthesized from the primer sequence position to the 5' end. Therefore, it was detected at a larger size position than the double-stranded 530-bp DNA by electrophoresis. As such, it was confirmed that a single-stranded DNA was able to be synthesized by PCR using human ET-3 cDNA as a template in the presence of a primer with only nine bases existing at one place of said template sequence.

(2) Amplification of 531 Bases in Human ET-3 cDNA by PCR.

A nucleotide sequence (5' C ATG GAG CC 3'; SEQ ID NO: 21) containing ATG codon which codes for methionine located at the 5'-side + strand of template precursor human ET-3 cDNA was used as a primer for one side whereby it was tried to confirm by PCR whether 422 base DNA was able to be amplified.

A PCR reaction solution was composed of:

25 pM (1 μl) of DNA primer having a nucleotide sequence of 5' C ATG GAG CC 3' (SEQ ID NO: 21)

and the reaction solution: Composition A as given in Example 1 (1) wherein the DNA primer was added to the solution:

Composition A. The final volume of the solution was made 100 μl.

The conditions for the PCR were:
Each cycle was consisted of incubation at 94° C. for 1 min., incubation at 36° C. for 1 min. and incubation at 72° C. for 2 min. and 46 cycles were conducted.

Figure 5:
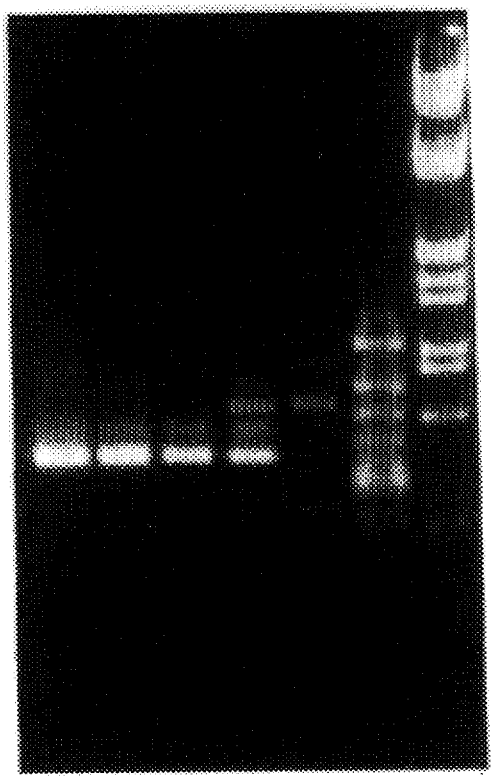
FIG. 5 is a photograph showing an electrophoresis profile of a product obtained by PCR using template human endothelin-3 cDNA. Lane 1 shows a sample obtained by PCR using 100 ng/100 µl of the template human endothelin-3 cDNA. Ten-fold dilutions of template human endothelin-3 cDNA (100 ng/ 100 µl) were made sequentially, and the serial template dilutions were subjected to PCR followed by running in lanes 2 to 5. Bands of the lanes 1 to 5 show band positions of the products. M1 shows a molecular marker of HincII-digested phage ø λ DNA174 fragments. M2 shows a marker of EcoRI/HindIII-digested phage λ DNA fragments.
Figure 6:
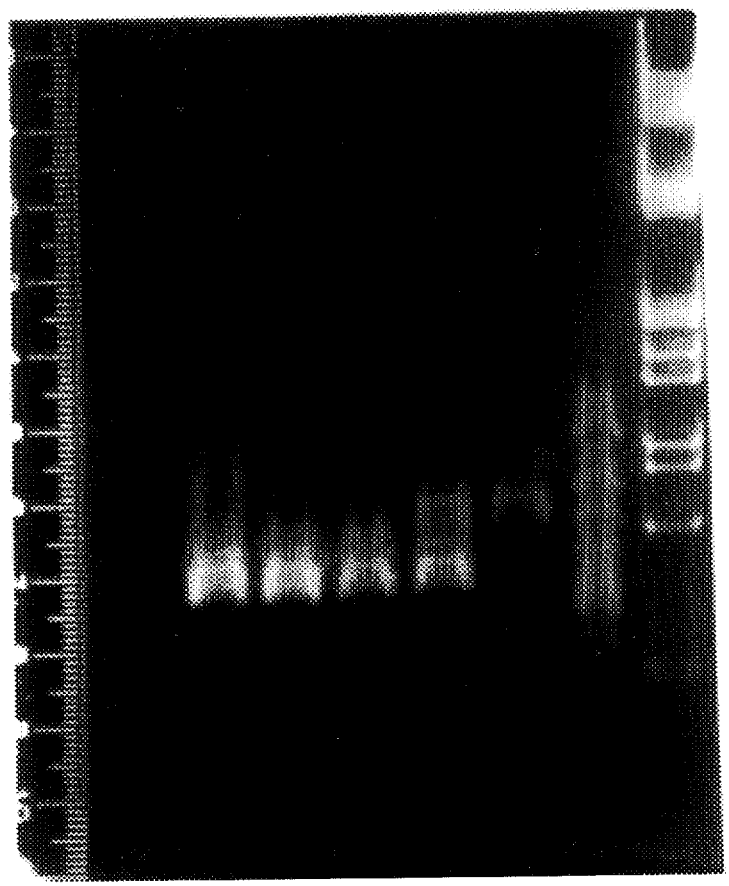
FIG. 6 is a photograph showing an electrophoresis profile of a product obtained by PCR for template human endothelin-3 cDNA. Lane 1 shows a product sample obtained by PCR using 100 ng/100 µl of template human endothelin-3 cDNA. Ten-fold dilutions of template human endothelin-3 cDNA (100 ng/100 µl) were made sequentially, and the serial template dilutions were subjected to PCR followed by running in lanes 2 to 5. The bands of the lanes 1 to 5 show band positions of the products. M1 shows a molecular marker of HincII-digested phage λ DNA174 fragments. M2 shows a molecular marker of EcoRI/HindIII-digested phage λ DNA fragments.

An aliquot (25 μl) of the reaction solution was analyzed by an agarose gel electrophoresis in the same manner as in Example 1 (1) and the results are given in FIG. 5 and in FIG. 6. It is clear from FIG. 5 and FIG. 6 that the main DNA synthesized upon the use of two sequences as primers was smaller in size than a molecular marker 580 base DNA fragment which is one of DNA fragments obtained by digestion of λ DNA with EcoRI and HindIII and it is clear that a DNA which is between the 495 base and the 392 base fragments obtained by digestion of phage ø λ 174 with HincII was synthesized. It is noted that this band was not observed in FIG. 3 which shows the result of Example 1.

Figure 7:
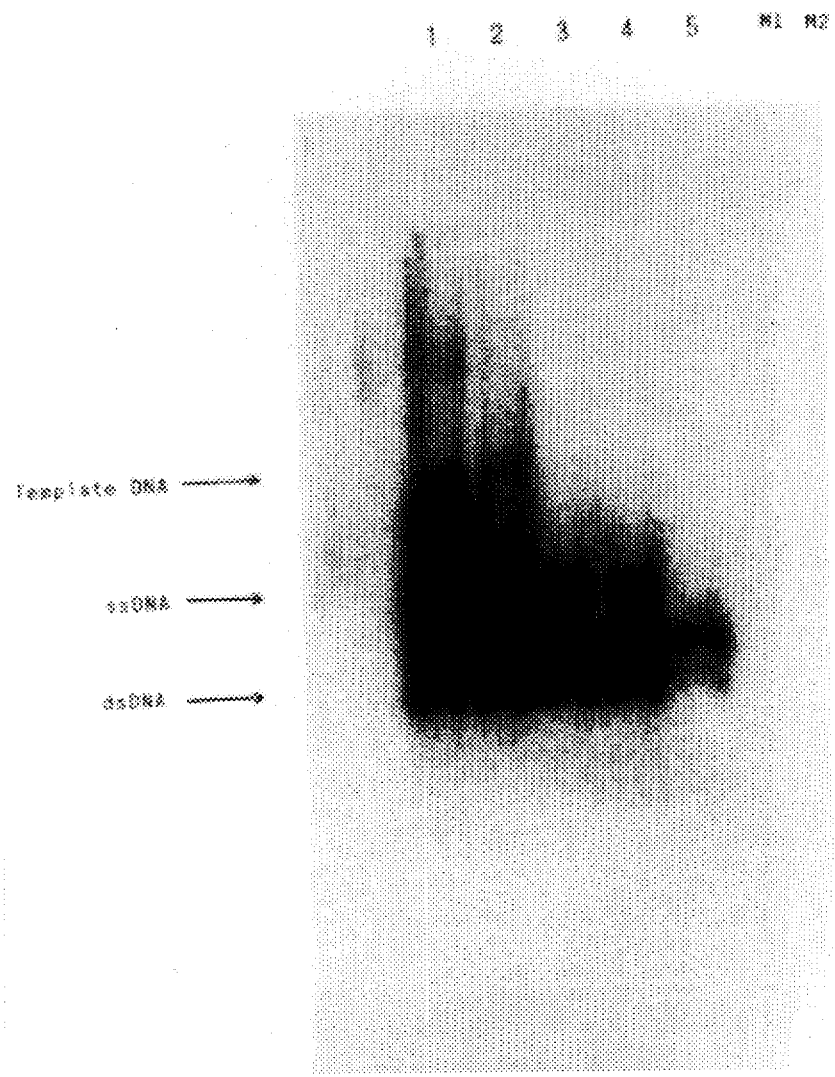
FIG. 7 is a photograph showing a southern hybridization profile of a double-stranded human endothelin-3 cDNA (dsDNA) and a single-stranded human endothelin-3 cDNA (ssDNA) in the products which were obtained by PCR using template human endothelin-3 cDNA with labeled human endothelin-3 cDNA. Lane 1 shows a product sample obtained by PCR using 100 ng/100 µl of template human endothelin-3 cDNA. Lane 2 shows a product sample obtained by PCR wherein 10-fold dilutions of 100 ng/100 µl of template human endothelin-3 cDNA were made sequentially and the resulting serial dilutions were subjected to an amplification. The bands of the lanes 1 to 5 show band positions of the products. M1 shows a molecular marker of HincII-digested phage λ DNA174 fragments. M2 shows a molecular marker of EcoRI/HindIII-digested phage λ DNA fragments.

This result indicates that its size corresponds to the length of the nucleotides lying between the two primer regions in the sequence of the human ET-3 cDNA. This synthesized DNA was investigated by a southern blotting and the result is given in FIG. 7. As shown in FIG. 7, it was observed that an intense band which is hybridized with the probe is present at a position corresponding to the near 422nd base. It is presumably determined that, at the position which corresponds to a bigger band, a single-stranded DNA and an unreacted template DNA are hybridized with the probe, respectively.

From the results of Examples 1 (1) and (2), it was proved that a desired DNA fragment can be amplified when the primer DNA fragment composed of nine bases is used.

The following example (Example 2) illustrates an embodiment in which a cDNA encoding a peptide comprising the two basic amino acid residues: Lys-Lys, Lys-Arg, Arg-Arg or Ser-Ser at the N-terminal side was amplified and cloned based upon the above-mentioned results.

Example 2

Screening of Human ET-3 cDNA from a cDNA Library.

A DNA having a nucleotide sequence which was complementary to DNA comprising a nucleotide sequence (with 9 nucleotides) coding for Gly-Lys-Arg was used as a primer for one side while a primer sequence near the cDNA cloning site of a plasmid or phage vector in which human ET-3 cDNA was integrated was used as a primer for another side.

For example, when PCR is carried out using, as a primer, a DNA having a sequence in pUC118 (e.g., SEQ ID NO: 15, SEQ ID NO: 16, etc.) or a DNA having a sequence in phage λ gt11 (e.g., SEQ ID NO: 13, SEQ ID NO: 14, etc.), it is presumed that a desired target DNA fragment (i.e., a DNA fragment comprising a nucleotide sequence which codes for Gly-Lys-Arg at the C-terminal side and comprising a nucleotide sequence which codes for the two basic amino acid residues, i.e. Lys-Lys, Lys-Arg, Arg-Arg or Ser-Ser, at the upstream region) will be amplified.

In order to prove the above presumption, an aliquot (20 μl: 10¹⁰ plaques/ml) of a cDNA library derived from human placenta (phage λ gt11 cDNA library) is suspended in 80 μl of distilled water and the mixture was heated at 98° C. for 10 min. to destroy the phage particles followed by rapidly cooling. An aliquot (10 μl) of the resulting solution was used as a decayed phage particle solution for PCR.

The PCR was carried out using a reaction solution of the following composition:

| Reaction Solution: Composition B: | |
|---|---|
| Decayed phage particle solution: | 10 μl |
| Phage λ gt11 DNA Primer: | 1 μl |
| 5' CCT CTT GCC 3' (SEQ ID NO: 20): | 1 μl |
| PCR × 10 Buffers: | 10 μl |
| dNTP Solution: 2.5 mM | 10 μl |
| Distilled water: | 66 μl |
| Taq Polymerase: | 2 μl |
| Total | 100 μl |

The PCR amplification was carried out for 46 cycles wherein each cycle consisted of incubation at 94° C. for 1 min., incubation at 36° C. for 1 min. and incubation at 72° C. for 2 min., incubation at 95° C. for I min., 55° C. for 2 min. and 72° C. for 2 min.

Figure 8:
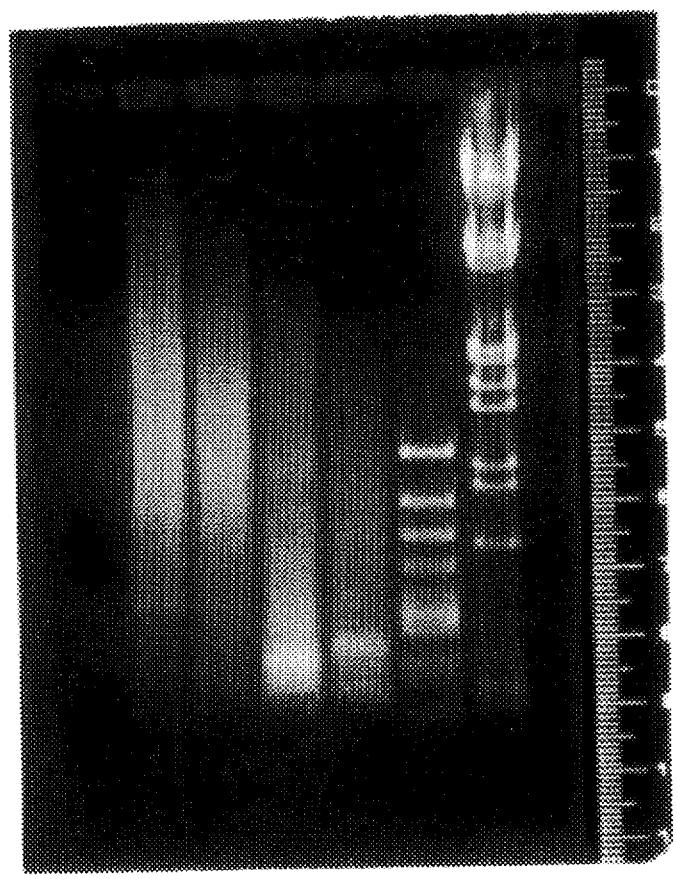
FIG. 8 is a photograph showing an electrophoresis profile of products obtained by PCR using various cDNA libraries as templates. Lanes 1 and 2 show electrophoresed PCR products obtained by using cDNA libraries (phage λ gt11 cDNA libraries) derived from human placenta. Lanes 3 and 4 show electrophoresed PCR products obtained by using, as a template, a cDNA library derived from human brain. M1 shows a molecular marker of HincII-digested phage ø λ DNA174 fragments. M2 shows a molecular marker of EcoRI/HindIII-digested phage λ DNA fragments.
Figure 9:
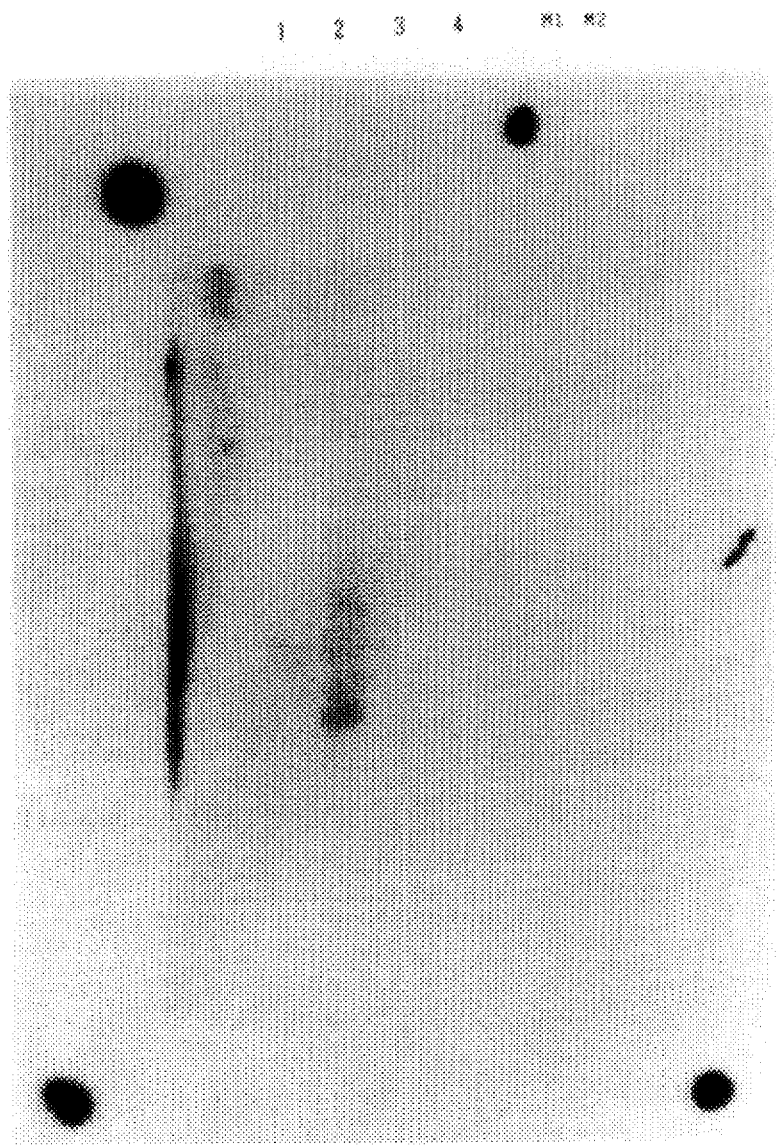
FIG. 9 is a photograph showing a southern hybridization profile of the product (which is obtained by PCR using various cDNA libraries as templates) with labeled human endothelin-3 cDNA. Lanes 1 and 2 show southern hybridized products (which are obtained by PCR using, as templates, cDNA libraries (phage λ gt11 cDNA libraries) derived from human placenta) bound with labeled human endothelin-3 cDNA. Lanes 3 and 4 show southern hybridized products (obtained by PCR using template cDNA libraries derived from human brain) bound with labeled human endothelin-3 cDNA. M1 shows a molecular marker of HincII-digested phage ø λ DNA174 fragments. M2 shows a molecular marker of EcORI/HindIII-digested phage λ DNA fragments.

An aliquot (20 μl) of the reaction solution was subjected to a 1% agarose gel electrophoresis and the DNA stained with ethidium bromide. The visualized pattern is shown in FIG. 8. It is apparent from FIG. 8 that DNA fragments of various sizes were synthesized. In order to confirm whether there is, for example, a human ET-3 cDNA among the synthesized DNAs, a southern blotting was conducted using the human ET-3 cDNA obtained in Example 1 as a probe. The result is given in FIG. 9. From FIG. 9, it was confirmed that an intense band which was clearly hybridized at the position near about 530 bases with the probe was observed in the amplified DNA.

From the above results, it was learned that the cDNA which codes for a peptide having an amino acid sequence of Gly-Lys-Arg at the C-terminal side was successfully amplified. In addition, it is possible to amplify cDNA having an amino acid sequence of Gly-Arg-Arg at the C-terminal side by the same method.

Example 3

Human poly(A) +RNA (Clontech, USA; mRNA isolated from cells of human pituitary gland, hypothalamus, brain, hippocampus, heart, kidney, lung, stomach, intestine, placenta and pancreas according to protocols utilizing guanidinium salts) was used as a template for synthesis of cDNA. Synthesis of cDNA was conducted by using, as primers, antisense codons for Gly-Arg-Arg, Gly-Lys-Arg and Gly-Lys-Lys, respectively. The cDNA product was ligated with EcoRI adaptors:

```
5' HO AA TTC GAG GAT CCG GGT ACC ATG G
      3'   G CTC CTA GGC CCA TGG TAC C OH
```
(SEQ ID NO: 22)

by a cDNA rapid adaptor ligation module (code RPN 1712, Amersham) followed by insertion into the EcoRI site of λ gt11 phage (Clontech, USA). The recombinant λ gt11 phage (containing the cDNA insert) was then packaged to form phage particles which are used to generate cDNA libraries.

Recombinant λ gt11 phage DNA with the cDNA insert was purified from the recombinant phages by the method described in Maniatis, et al., "Molecular Cloning" 2nd edition, Cold Spring Harbor Laboratory Press, 1989 and then extracted by the method described in Maniatis, et al., ibid., which is incorporated herein by reference.

The purified recombinant λ gt11 phage DNA was subjected to PCR amplification using λ gt11 primers (TAKARA catalogs No. 3865 & 3866, Takara Shuzo Co., Ltd., Japan:

Forward Primer:
  5' GGTGGCGACGACTCCTGGAGCCCG 3'
(SEQ ID NO: 23)
or
Reverse Primer:
  5' TTGACACCAGACCAACTGGTAATG '
(SEQ ID NO: 24))

and primers having each antisense codon for Gly-Arg-Arg, Gly-Lys-Arg or Gly-Lys-Lys as mentioned hereinabove. The PCR amplification was conducted in the same manner as in Example 1.

The PCR product was subcloned with a TA receptor (TA cloning kit, Invitrogen, USA) and cDNA fragments from 100 clones were sequenced.

Among the clones, it was learned that clone No. 99 had a portion of cDNA coding for human proopiomelanocortin (DNA, Vol. 1, 133–143, 1982) which was a peptide hormone precursor, also included an entire sequence of cDNA coding for γ-MSH (DNA, Vol. 1, 133–143, 1982) and possessed a nucleotide sequence identical with the 5' upstream region of GRR (Gly-Arg-Arg).

The nucleotide sequence of clone No. 99 is shown in FIG. 10. Among the amino acid sequences shown in FIG. 10, the middle amino acid sequence represents a coding sequence wherein the DNA was read in one reading frame by shifting the reading frame coding for the bottom amino acid sequence by one base and the top amino acid sequence represents a coding sequence wherein the DNA was read in another reading frame by shifting by further one base the reading frame coding for the middle amino acid sequence. FIG. 11 depicts a nucleotide sequence of clone No. 99 and a region ranging from the 1st to the 255th residues at the N terminal of human proopiomelanocortin-coding cDNA, wherein both sequences are arranged side by side in a row (the upper sequence represents the nucleotide sequence of clone No. 99 and the lower sequence represents the cDNA sequence coding for human proopiomelanocortin). FIG. 12 depicts the amino acid sequence of human proopiomelanocortin. In FIG. 12, the amino acid sequence encoded by the clone No. 99 cDNA corresponds to a region ranging from the −21st to the −1st amino acid residues of the signal region of human proopiomelanocortin and from the 1st to the 64th amino acid residues of the coding region thereof.

What is claimed is:

1. A hormone or hormone-precursor detecting DNA primer for use in detecting hormones or hormone-precursors, comprising a nucleotide sequence having 9 or more nucleotides complementary to a polynucleotide containing a nucleotide sequence coding for Gly-Lys-Arg, Gly-Arg-Arg or Gly-Lys-Lys selected from the group consisting of SEQ ID No. 1, 2, 3, 4 or 5, provided that the nucleotide sequence of the DNA primer does not encode a native hormone or hormone-precursor.

2. A method for amplifying a polynucleotide containing a nucleotide sequence coding for Gly-Lys-Arg, Gly-Arg-Arg or Gly-Lys-Lys selected from the group consisting of SEQ ID No. 1, 2, 3, 4 or 5, which comprises conducting a polymerase chain reaction in the presence of, as a member of a primer pair, the DNA primer according to claim 1.

3. A screening method for a polynucleotide encoding an unknown hormone or hormone-precursor containing a nucleotide sequence coding for Gly-Lys-Arg, Gly-Arg-Arg or Gly-Lys-Lys selected from the group consisting of SEQ ID No. 1, 2, 3, 4 or 5, which comprises conducting a polymerase chain reaction in the presence of, as a member of a primer pair, the DNA primer according to claim 1, and amplifying selectively said polynucleotide.

4. A screening method for an unknown hormone or hormone-precursor, which comprises (1) screening for a polynucleotide containing a nucleotide sequence coding for C-terminal amino acids Gly-Lys-Arg, Gly-Arg-Arg or Gly-Lys-Lys selected from the group consisting of SEQ ID No. 1, 2, 3, 4 or 5; and (2) screening for a polynucleotide containing a nucleotide sequence coding for N-terminal amino acids Lys-Lys, Lys-Arg, Arg-Arg or Ser-Ser.

5. A hormone or hormone-precursor detecting DNA primer for use in detecting hormone or hormone-precursors, which comprises a nucleotide sequence represented by a SEQ ID No. selected from the group consisting of SEQ ID No. 6 to SEQ ID No. 10.

6. A hormone or hormone-precursor detecting DNA primer for use in detecting hormone or hormone-precursors, which comprises a nucleotide sequence represented by SEQ ID No. 20.

* * * * *

SEQUENCE LISTING ( 1 ) GENERAL INFORMATION:

( i i i ) NUMBER OF SEQUENCES: 24

( 2 ) INFORMATION FOR SEQ ID NO: 1:

( i ) SEQUENCE CHARACTERISTICS:
    ( A ) LENGTH: 9

( B ) TYPE: Nucleic acid
( C ) STRANDEDNESS: Single
( D ) TOPOLOGY: Linear ( i i ) MOLECULE TYPE: Other nucleic acid
Synthetic DNA ( x i ) SEQUENCE DESCRIPTION: SEQ ID NO: 1:

GGNAARCGN 9

( 2 ) INFORMATION FOR SEQ ID NO: 2:

( i ) SEQUENCE CHARACTERISTICS:
( A ) LENGTH: 9
( B ) TYPE: Nucleic acid
( C ) STRANDEDNESS: Single
( D ) TOPOLOGY: Linear ( i i ) MOLECULE TYPE: Other nucleic acid
Synthetic DNA ( x i ) SEQUENCE DESCRIPTION: SEQ ID NO: 2:

GGNAARAGR 9

( 2 ) INFORMATION FOR SEQ ID NO: 3:

( i ) SEQUENCE CHARACTERISTICS:
( A ) LENGTH: 9
( B ) TYPE: Nucleic acid
( C ) STRANDEDNESS: Single
( D ) TOPOLOGY: Linear ( i i ) MOLECULE TYPE: Other nucleic acid
Synthetic DNA ( x i ) SEQUENCE DESCRIPTION: SEQ ID NO: 3:

GGNCGNCGN 9

( 2 ) INFORMATION FOR SEQ ID NO: 4:

( i ) SEQUENCE CHARACTERISTICS:
( A ) LENGTH: 9
( B ) TYPE: Nucleic acid
( C ) STRANDEDNESS: Single
( D ) TOPOLOGY: Linear ( i i ) MOLECULE TYPE: Other nucleic acid
Synthetic DNA ( x i ) SEQUENCE DESCRIPTION: SEQ ID NO: 4:

GGNAGRAGR 9

( 2 ) INFORMATION FOR SEQ ID NO: 5:

( i ) SEQUENCE CHARACTERISTICS:
( A ) LENGTH: 9
( B ) TYPE: Nucleic acid
( C ) STRANDEDNESS: Single
( D ) TOPOLOGY: Linear ( i i ) MOLECULE TYPE: Other nucleic acid
Synthetic DNA ( x i ) SEQUENCE DESCRIPTION: SEQ ID NO: 5:

GGNAARAAR 9

( 2 ) INFORMATION FOR SEQ ID NO: 6:

( i ) SEQUENCE CHARACTERISTICS:
( A ) LENGTH: 9

(B) TYPE: Nucleic acid
(C) STRANDEDNESS: Single
(D) TOPOLOGY: Linear (ii) MOLECULE TYPE: Other nucleic acid
Synthetic DNA (xi) SEQUENCE DESCRIPTION: SEQ ID NO: 6:

NCGYTTNCC 9

(2) INFORMATION FOR SEQ ID NO: 7:

(i) SEQUENCE CHARACTERISTICS:
(A) LENGTH: 9
(B) TYPE: Nucleic acid
(C) STRANDEDNESS: Single
(D) TOPOLOGY: Linear (ii) MOLECULE TYPE: Other nucleic acid
Synthetic DNA (xi) SEQUENCE DESCRIPTION: SEQ ID NO: 7:

YCTYTTNCC 9

(2) INFORMATION FOR SEQ ID NO: 8:

(i) SEQUENCE CHARACTERISTICS:
(A) LENGTH: 9
(B) TYPE: Nucleic acid
(C) STRANDEDNESS: Single
(D) TOPOLOGY: Linear (ii) MOLECULE TYPE: Other nucleic acid
Synthetic DNA (xi) SEQUENCE DESCRIPTION: SEQ ID NO: 8:

NCGNCGNCC 9

(2) INFORMATION FOR SEQ ID NO: 9:

(i) SEQUENCE CHARACTERISTICS:
(A) LENGTH: 9
(B) TYPE: Nucleic acid
(C) STRANDEDNESS: Single
(D) TOPOLOGY: Linear (ii) MOLECULE TYPE: Other nucleic acid
Synthetic DNA (xi) SEQUENCE DESCRIPTION: SEQ ID NO: 9:

YCTYCTNCC 9

(2) INFORMATION FOR SEQ ID NO: 10:

(i) SEQUENCE CHARACTERISTICS:
(A) LENGTH: 9
(B) TYPE: Nucleic acid
(C) STRANDEDNESS: Single
(D) TOPOLOGY: Linear (ii) MOLECULE TYPE: Other nucleic acid
Synthetic DNA (xi) SEQUENCE DESCRIPTION: SEQ ID NO: 10:

YTTYTTNCC 9

(2) INFORMATION FOR SEQ ID NO: 11:

(i) SEQUENCE CHARACTERISTICS:
(A) LENGTH: 20

( B ) TYPE: Nucleic acid
( C ) STRANDEDNESS: Single
( D ) TOPOLOGY: Linear ( i i ) MOLECULE TYPE: Other nucleic acid
Synthetic DNA ( x i ) SEQUENCE DESCRIPTION: SEQ ID NO: 11:

GCTGGGTAGT CCCCACCTTT                                                                       20

( 2 ) INFORMATION FOR SEQ ID NO: 12:

( i ) SEQUENCE CHARACTERISTICS:
( A ) LENGTH: 24
( B ) TYPE: Nucleic acid
( C ) STRANDEDNESS: Single
( D ) TOPOLOGY: Linear ( i i ) MOLECULE TYPE: Other nucleic acid
Synthetic DNA ( x i ) SEQUENCE DESCRIPTION: SEQ ID NO: 12:

CTTATGAGTA TTTCTTCCAG GGTA                                                                  24

( 2 ) INFORMATION FOR SEQ ID NO: 13:

( i ) SEQUENCE CHARACTERISTICS:
( A ) LENGTH: 24
( B ) TYPE: Nucleic acid
( C ) STRANDEDNESS: Single
( D ) TOPOLOGY: Linear ( i i ) MOLECULE TYPE: Other nucleic acid
Synthetic DNA ( x i ) SEQUENCE DESCRIPTION: SEQ ID NO: 13:

GGTGGCGACG ACTCCTGGAG CCCG                                                                  24

( 2 ) INFORMATION FOR SEQ ID NO: 14:

( i ) SEQUENCE CHARACTERISTICS:
( A ) LENGTH: 24
( B ) TYPE: Nucleic acid
( C ) STRANDEDNESS: Single
( D ) TOPOLOGY: Linear ( i i ) MOLECULE TYPE: Other nucleic acid
Synthetic DNA ( x i ) SEQUENCE DESCRIPTION: SEQ ID NO: 14:

TTGACACCAG ACCAACTGGT AATG                                                                  24

( 2 ) INFORMATION FOR SEQ ID NO: 15:

( i ) SEQUENCE CHARACTERISTICS:
( A ) LENGTH: 16
( B ) TYPE: Nucleic acid
( C ) STRANDEDNESS: Single
( D ) TOPOLOGY: Linear ( i i ) MOLECULE TYPE: Other nucleic acid
Synthetic DNA ( x i ) SEQUENCE DESCRIPTION: SEQ ID NO: 15:

CAGGAAACAG CTATGA                                                                           16

( 2 ) INFORMATION FOR SEQ ID NO: 16:

( i ) SEQUENCE CHARACTERISTICS:
( A ) LENGTH: 17

( B ) TYPE: Nucleic acid
            ( C ) STRANDEDNESS: Single
            ( D ) TOPOLOGY: Linear ( i i ) MOLECULE TYPE: Other nucleic acid
            Synthetic DNA ( x i ) SEQUENCE DESCRIPTION: SEQ ID NO: 16:

GTCGTGACTG GGAAAAC                                                                              17

( 2 ) INFORMATION FOR SEQ ID NO: 17:

( i ) SEQUENCE CHARACTERISTICS:
                ( A ) LENGTH: 17
                ( B ) TYPE: Nucleic acid
                ( C ) STRANDEDNESS: Single
                ( D ) TOPOLOGY: Linear ( i i ) MOLECULE TYPE: Other nucleic acid
                Synthetic DNA ( x i ) SEQUENCE DESCRIPTION: SEQ ID NO: 17:

AATACGACTC ACTATAG                                                                              17

( 2 ) INFORMATION FOR SEQ ID NO: 18:

( i ) SEQUENCE CHARACTERISTICS:
                ( A ) LENGTH: 18
                ( B ) TYPE: Nucleic acid
                ( C ) STRANDEDNESS: Single
                ( D ) TOPOLOGY: Linear ( i i ) MOLECULE TYPE: Other nucleic acid
                Synthetic DNA ( x i ) SEQUENCE DESCRIPTION: SEQ ID NO: 18:

ATTTAGGTGA CACTATAG                                                                             18

( 2 ) INFORMATION FOR SEQ ID NO: 19:

( i ) SEQUENCE CHARACTERISTICS:
                ( A ) LENGTH: 9
                ( B ) TYPE: Nucleic acid
                ( C ) STRANDEDNESS: Single
                ( D ) TOPOLOGY: Linear ( i i ) MOLECULE TYPE: Other nucleic acid
                Synthetic DNA ( x i ) SEQUENCE DESCRIPTION: SEQ ID NO: 19:

GGCAAGAGG                                                                                        9

( 2 ) INFORMATION FOR SEQ ID NO: 20:

( i ) SEQUENCE CHARACTERISTICS:
                ( A ) LENGTH: 9
                ( B ) TYPE: Nucleic acid
                ( C ) STRANDEDNESS: Single
                ( D ) TOPOLOGY: Linear ( i i ) MOLECULE TYPE: Other nucleic acid
                Synthetic DNA ( x i ) SEQUENCE DESCRIPTION: SEQ ID NO: 20:

CCTCTTGCC                                                                                        9

( 2 ) INFORMATION FOR SEQ ID NO: 21:

( i ) SEQUENCE CHARACTERISTICS:
                ( A ) LENGTH: 9

( B ) TYPE: Nucleic acid
        ( C ) STRANDEDNESS: Single
        ( D ) TOPOLOGY: Linear ( i i ) MOLECULE TYPE: Other nucleic acid
            Synthetic DNA ( x i ) SEQUENCE DESCRIPTION: SEQ ID NO: 21:

CATGGAGCC 9

( 2 ) INFORMATION FOR SEQ ID NO: 22:

( i ) SEQUENCE CHARACTERISTICS:
        ( A ) LENGTH: 24
        ( B ) TYPE: Nucleic acid
        ( C ) STRANDEDNESS: Double
        ( D ) TOPOLOGY: Linear ( i i ) MOLECULE TYPE: Other nucleic acid
            Synthetic DNA ( x i ) SEQUENCE DESCRIPTION: SEQ ID NO: 22:

AATTCGAGGA TCCGGGTACC ATGG 24

( 2 ) INFORMATION FOR SEQ ID NO: 23:

( i ) SEQUENCE CHARACTERISTICS:
        ( A ) LENGTH: 24
        ( B ) TYPE: Nucleic acid
        ( C ) STRANDEDNESS: Single
        ( D ) TOPOLOGY: Linear ( i i ) MOLECULE TYPE: Other nucleic acid
            Synthetic DNA ( x i ) SEQUENCE DESCRIPTION: SEQ ID NO: 23:

GGTGGCGACG ACTCCTGGAG CCCG 24

( 2 ) INFORMATION FOR SEQ ID NO:24:

( i ) SEQUENCE CHARACTERISTICS:
        ( A ) LENGTH: 24
        ( B ) TYPE: Nucleic acid
        ( C ) STRANDEDNESS: Single
        ( D ) TOPOLOGY: Linear ( i i ) MOLECULE TYPE: Other nucleic acid
            Synthetic DNA ( x i ) SEQUENCE DESCRIPTION: SEQ ID NO:24:

TTGACACCAG ACCAACTGGT AATG 24